(12) United States Patent
Won et al.

(10) Patent No.: US 12,005,082 B2
(45) Date of Patent: Jun. 11, 2024

(54) COMPOSITION AND METHOD OF USE RECOMBINANT FUSION PROTEIN TO GENERATE CAR-IMMUNE CELLS

(71) Applicant: SINGULAR IMMUNE, INC., Dallas, TX (US)

(72) Inventors: Youngwook Won, Southlake, TX (US); Seungmin Han, Denton, TX (US); David Bull, Salt Lake City, UT (US)

(73) Assignee: SINGULAR IMMUNE, INC., Dallas, TX (US)

( * ) Notice: Subject to any disclaimer, the term of this patent is extended or adjusted under 35 U.S.C. 154(b) by 0 days.

(21) Appl. No.: 18/185,805

(22) Filed: Mar. 17, 2023

(65) Prior Publication Data
US 2023/0293584 A1 Sep. 21, 2023

Related U.S. Application Data

(60) Provisional application No. 63/320,885, filed on Mar. 17, 2022.

(51) Int. Cl.
*A61K 35/17* (2015.01)
*A61P 35/00* (2006.01)
*C07K 14/725* (2006.01)
*C07K 16/28* (2006.01)

(52) U.S. Cl.
CPC .............. *A61K 35/17* (2013.01); *A61P 35/00* (2018.01); *C07K 14/7051* (2013.01); *C07K 16/2827* (2013.01)

(58) Field of Classification Search
CPC .... A61K 35/17; A61K 39/46; A61K 39/4613; A61K 39/4631; A61P 35/00; C07K 14/7051; C07K 16/2827; C07K 16/2803; C07K 2319/50
See application file for complete search history.

(56) References Cited

U.S. PATENT DOCUMENTS 10,822,419 B2    11/2020    Wang et al.
2018/0251521 A1   9/2018    LaFleur et al.

FOREIGN PATENT DOCUMENTS

WO    2018/201056 A1    11/2018

OTHER PUBLICATIONS

International Search Report and Written Opinion of the International Searching Authority mailed Jul. 5, 2023 for related PCT/US23/15470.
Louai Labanieh et al., "Programming CAR-T cells to kill cancer" Nature Biomedical Engineering; vol. 2, No. 6, Jun. 11, 2018; pp. 377-391; DOI: https://doi.org/10.1038/s41551-018-0235-9.

*Primary Examiner* — Nelson B Moseley, II
*Assistant Examiner* — Alyssa Rae Stonebraker
(74) *Attorney, Agent, or Firm* — Sughrue Mion, PLLC

(57) ABSTRACT

Provided herein are a recombinant chimeric antigen receptor (CAR) fusion protein, a method of modifying an immune cell into a CAR immune cell by treating the immune cell with the recombinant CAR fusion protein, and a method of treating cancer by administering the CAR immune cell to a subject in need thereof.

16 Claims, 25 Drawing Sheets

Specification includes a Sequence Listing.

FIG. 1

SEQ ID NO: 1

MEVQLQQSGPELVKPGASVKISCKTSGYTFTEYTMHWVKQSHGKSLEWI
GGISPNIGGTSYNQKFKGKATLTVDKSSSTAYMELRSLTSEDSAVYYCARRGGSF
DYWGQGTTLTVSSEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQ
QGNVFSCSVMHEALHNHYTQKSLSLSPGK*GGGGSGGGGSGGGGS*RRAR*MALPVT
ALLLPLALLLHAARP*EVQLVESGGGLVQPGGSLRLSCAASGFTFSDSWIHWVRQAPGK
GLEWVAWISPYGGSTYYADSVKGRFTISADTSKNTAYLQMNSLRAEDTAVYYCARR
HWPGGFDYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVD
KKVEPKSCDKTHTCPPCPAPELLGGPSVFLFPPKPKDTLMISRTPEVTCVVVDVSHED
PEVKFNWYVDGVEVHNAKTKPREEQYASTYRVVSVLTVLHQDWLNGKEYKCKVS
NKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQ
KSLSLSPGK*FVPVFLPAKPTTTPAPRPPTPAPTIASQPLSLRPEACRPAAGGAVHTRGL
DFACD*PFFFCCFIAVAMGIRFIIMVAWRRKAKEKQSETSPKEFLTIYEDVKDLKTRRNHEQEQTF
PGGGSTIYSMIQSQSSAPTSQEPAYTLYSLIQPSRKSGSRKRNHSPSFNSTIYEVIGKSQPKAQNPARLSRK
ELENFDVYSRVKFSRSADAPAYQQGQNQLYNELNLGRREEYDVLDKRRGRDPEMGGKPQRRKNPQE
GLYNELQKDKMAEAYSEIGMKGERRRGKGHDGLYQGLSTATKDTYDALHMQALPPR*GGGGS*HHH
HHH

SDS-PAGE & Western blot Analysis:

Lane $M_1$ : Protein marker, Bio-rad, Cat. No. 1610374S, refer to annotated key on the left for size Lane $M_2$ : Protein marker, GenScript, Cat. No. M00673, refer to annotated key on the left for size BSA : 2.00 µg R : Reducing condition Primary antibody : Mouse-anti-His mAb (Genscript, Cat.No. A00186)

Vehicle (Control)-treated mice

- 16.82% Human NK
- 2.14% Human CD8+ T
- 3.69% Human CD4+ T
- 16.46% Human Macrophage
- 60.89% Mouse immune cells

In vivo CAR PD-L1 (1.7mg/Kg)-treated mice

- 19.03% Human NK
- 4.67% Human CD8+ T
- 1.12% Human CD4+ T
- 17.40% Human Macrophage
- 57.78% Mouse immune cells

In vivo CAR PD-L1 (11mg/Kg)-treated mice

- 20.59% Human NK
- 5.81% Human CD8+ T
- 0.81% Human CD4+ T
- 19.93% Human Macrophage
- 52.87% Mouse immune cells

```
                               SEQUENCE LISTING

Sequence total quantity: 79
SEQ ID NO: 1            moltype = AA  length = 1157
FEATURE                 Location/Qualifiers
REGION                  1..1157
                        note = peptide
source                  1..1157
                        mol_type = protein
                        organism = synthetic construct
SEQUENCE: 1
MEVQLQQSGP ELVKPGASVK ISCKTSGYTF TEYTMHWVKQ SHGKSLEWIG GISPNIGGTS    60
YNQKFKGKAT LTVDKSSSTA YMELRSLTSE DSAVYYCARR GGSFDYWGQG TTLTVSSEPK   120
SCDKTHTCPP CPAPELLGGP SVFLFPPKPK DTLMISRTPE VTCVVVDVSH EDPEVKFNWY   180
VDGVEVHNAK TKPREEQYNS TYRVVSVLTV LHQDWLNGKE YKCKVSNKAL PAPIEKTISK   240
AKGQPREPQV YTLPPSRDEL TKNQVSLTCL VKGFYPSDIA VEWESNGQPE NNYKTTPPVL   300
DSDGSFFLYS KLTVDKSRWQ QGNVFSCSVM HEALHNHYTQ KSLSLSPGKG GGGSGGGGSG   360
GGGSRRARMA LPVTALLLPL ALLLHAARPE VQLVESGGGL VQPGGSLRLS CAASGFTFSD   420
SWIHWVRQAP GKGLEWVAWI SPYGGSTYYA DSVKGRFTIS ADTSKNTAYL QMNSLRAEDT   480
AVYYCARRHW PGGFDYWGQG TLVTVSSAST KGPSVFPLAP SSKSTSGGTA ALGCLVKDYF   540
PEPVTVSWNS GALTSGVHTF PAVLQSSGLY SLSSVVTVPS SSLGTQTYIC NVNHKPSNTK   600
VDKKVEPKSC DKTHTCPPCP APELLGGPSV FLFPPKPKDT LMISRTPEVT CVVVDVSHED   660
PEVKFNWYVD GVEVHNAKTK PREEQYASTY RVVSVLTVLH QDWLNGKEYK CKVSNKALPA   720
PIEKTISKAK GQPREPQVYT LPPSREEMTK NQVSLTCLVK GFYPSDIAVE WESNGQPENN   780
YKTTPPVLDS DGSFFLYSKL TVDKSRWQQG NVFSCSVMHE ALHNHYTQKS LSLSPGKFVP   840
VFLPAKPTTT PAPRPPTPAP TIASQPLSLR PEACRPAAGG AVHTRGLDFA CDPFFFCCFI   900
AVAMGIRFII MVAWRRKAKE KQSETSPKEF LTIYEDVKDL KTRRNHEQEQ TFPGGGSTIY   960
SMIQSQSSAP TSQEPAYTLY SLIQPSRKSG SRKRNHSPSF NSTIYEVIGK SQPKAQNPAR  1020
LSRKELENFD VYSRVKFSRS ADAPAYQQGQ NQLYNELNLG RREEYDVLDK RRGRDPEMGG  1080
KPQRRKNPQE GLYNELQKDK MAEAYSEIGM KGERRRGKGH DGLYQGLSTA TKDTYDALHM  1140
QALPPRGGGG SHHHHHH                                                 1157

SEQ ID NO: 2            moltype = AA  length = 11
FEATURE                 Location/Qualifiers
REGION                  1..11
                        note = peptide
source                  1..11
                        mol_type = protein
                        organism = synthetic construct
SEQUENCE: 2
YGRKKRRQRR R                                                         11

SEQ ID NO: 3            moltype = AA  length = 9
FEATURE                 Location/Qualifiers
REGION                  1..9
                        note = peptide
source                  1..9
                        mol_type = protein
                        organism = synthetic construct
SEQUENCE: 3
RKKRRQRRR                                                             9

SEQ ID NO: 4            moltype = AA  length = 6
FEATURE                 Location/Qualifiers
REGION                  1..6
                        note = peptide
source                  1..6
                        mol_type = protein
                        organism = synthetic construct
SEQUENCE: 4
RRRRRR                                                                6

SEQ ID NO: 5            moltype = AA  length = 8
FEATURE                 Location/Qualifiers
REGION                  1..8
                        note = peptide
source                  1..8
                        mol_type = protein
                        organism = synthetic construct
SEQUENCE: 5
RRRRRRRR                                                              8

SEQ ID NO: 6            moltype = AA  length = 9
FEATURE                 Location/Qualifiers
REGION                  1..9
```

```
                                note          = peptide
source                          1..9
                                mol_type      = protein
                                organism      = synthetic construct
SEQUENCE: 6
RRRRRRRRR                                                                              9

SEQ ID NO: 7                    moltype = AA   length = 14
FEATURE                         Location/Qualifiers
REGION                          1..14
                                note          = peptide
source                          1..14
                                mol_type      = protein
                                organism      = synthetic construct
SEQUENCE: 7
RQIKIWFQNR RMKW                                                                        14

SEQ ID NO: 8                    moltype = AA   length = 16
FEATURE                         Location/Qualifiers
REGION                          1..16
                                note          = peptide
source                          1..16
                                mol_type      = protein
                                organism      = synthetic construct
SEQUENCE: 8
RQIKIWFQNR RMKWKK                                                                      16

SEQ ID NO: 9                    moltype = AA   length = 18
FEATURE                         Location/Qualifiers
REGION                          1..18
                                note          = peptide
source                          1..18
                                mol_type      = protein
                                organism      = synthetic construct
SEQUENCE: 9
VRLPPPVRLP PPVRLPPP                                                                    18

SEQ ID NO: 10                   moltype = AA   length = 12
FEATURE                         Location/Qualifiers
REGION                          1..12
                                note          = peptide
source                          1..12
                                mol_type      = protein
                                organism      = synthetic construct
SEQUENCE: 10
RRQRRTSKLM KR                                                                          12

SEQ ID NO: 11                   moltype = AA   length = 16
FEATURE                         Location/Qualifiers
REGION                          1..16
                                note          = peptide
source                          1..16
                                mol_type      = protein
                                organism      = synthetic construct
SEQUENCE: 11
AAVALLPAVL LALLAP                                                                      16

SEQ ID NO: 12                   moltype = AA   length = 17
FEATURE                         Location/Qualifiers
REGION                          1..17
                                note          = peptide
source                          1..17
                                mol_type      = protein
                                organism      = synthetic construct
SEQUENCE: 12
TRQARRNRRR RWRERQR                                                                     17

SEQ ID NO: 13                   moltype = AA   length = 15
FEATURE                         Location/Qualifiers
REGION                          1..15
                                note          = peptide
source                          1..15
                                mol_type      = protein
                                organism      = synthetic construct
SEQUENCE: 13
RRRRNRTRRN RRRVR                                                                       15

SEQ ID NO: 14                   moltype = AA   length = 13
FEATURE                         Location/Qualifiers
```

```
REGION                    1..13
                          note = peptide
source                    1..13
                          mol_type = protein
                          organism = synthetic construct
SEQUENCE: 14
TRRQRTRRAT TNR                                                              13

SEQ ID NO: 15             moltype = AA  length = 16
FEATURE                   Location/Qualifiers
REGION                    1..16
                          note = peptide
source                    1..16
                          mol_type = protein
                          organism = synthetic construct
SEQUENCE: 15
KRPAAIKKAG QAKKKK                                                           16

SEQ ID NO: 16             moltype = AA  length = 27
FEATURE                   Location/Qualifiers
REGION                    1..27
                          note = peptide
source                    1..27
                          mol_type = protein
                          organism = synthetic construct
SEQUENCE: 16
GWTLNSAGYL LGKINLKALA ALAKKIL                                               27

SEQ ID NO: 17             moltype = AA  length = 18
FEATURE                   Location/Qualifiers
REGION                    1..18
                          note = peptide
source                    1..18
                          mol_type = protein
                          organism = synthetic construct
SEQUENCE: 17
LLIILRRRIR KQAHAHSK                                                         18

SEQ ID NO: 18             moltype = AA  length = 14
FEATURE                   Location/Qualifiers
REGION                    1..14
                          note = peptide
source                    1..14
                          mol_type = protein
                          organism = synthetic construct
SEQUENCE: 18
YGRKKRRQRR RPPQ                                                             14

SEQ ID NO: 19             moltype = AA  length = 16
FEATURE                   Location/Qualifiers
REGION                    1..16
                          note = peptide
source                    1..16
                          mol_type = protein
                          organism = synthetic construct
SEQUENCE: 19
RQIKIWFQNR RMKWKK                                                           16

SEQ ID NO: 20             moltype = AA  length = 26
FEATURE                   Location/Qualifiers
REGION                    1..26
                          note = peptide
source                    1..26
                          mol_type = protein
                          organism = synthetic construct
SEQUENCE: 20
GWTLNSAGYL LGKINLKALA ALAKKL                                                26

SEQ ID NO: 21             moltype = AA  length = 7
FEATURE                   Location/Qualifiers
REGION                    1..7
                          note = peptide
source                    1..7
                          mol_type = protein
                          organism = synthetic construct
SEQUENCE: 21
LCLRPVG                                                                      7

SEQ ID NO: 22             moltype = AA  length = 10
```

-continued

```
FEATURE              Location/Qualifiers
REGION               1..10
                     note = peptide
source               1..10
                     mol_type = protein
                     organism = synthetic construct
SEQUENCE: 22
RRRRRRRRRR                                                                      10

SEQ ID NO: 23        moltype = AA  length = 10
FEATURE              Location/Qualifiers
REGION               1..10
                     note = peptide
source               1..10
                     mol_type = protein
                     organism = synthetic construct
SEQUENCE: 23
KKKKKKKKKK                                                                      10

SEQ ID NO: 24        moltype = AA  length = 18
FEATURE              Location/Qualifiers
REGION               1..18
                     note = peptide
source               1..18
                     mol_type = protein
                     organism = synthetic construct
SEQUENCE: 24
KLALKLALKA LKAALKLA                                                             18

SEQ ID NO: 25        moltype = AA  length = 21
FEATURE              Location/Qualifiers
REGION               1..21
                     note = peptide
source               1..21
                     mol_type = protein
                     organism = synthetic construct
SEQUENCE: 25
KETWWETWWT EWSQPKKKRK V                                                         21

SEQ ID NO: 26        moltype = AA  length = 12
FEATURE              Location/Qualifiers
REGION               1..12
                     note = peptide
source               1..12
                     mol_type = protein
                     organism = synthetic construct
SEQUENCE: 26
PLILLRLLRG QF                                                                   12

SEQ ID NO: 27        moltype = AA  length = 12
FEATURE              Location/Qualifiers
REGION               1..12
                     note = peptide
source               1..12
                     mol_type = protein
                     organism = synthetic construct
SEQUENCE: 27
PLIYLRLLRG QF                                                                   12

SEQ ID NO: 28        moltype = AA  length = 15
FEATURE              Location/Qualifiers
REGION               1..15
                     note = peptide
source               1..15
                     mol_type = protein
                     organism = synthetic construct
SEQUENCE: 28
KLWMRWYSPT TRRYG                                                                15

SEQ ID NO: 29        moltype = AA  length = 18
FEATURE              Location/Qualifiers
REGION               1..18
                     note = peptide
source               1..18
                     mol_type = protein
                     organism = synthetic construct
SEQUENCE: 29
KLALKLALKA LKAALKLA                                                             18
```

```
SEQ ID NO: 30          moltype = AA  length = 18
FEATURE                Location/Qualifiers
REGION                 1..18
                       note = peptide
source                 1..18
                       mol_type = protein
                       organism = synthetic construct
SEQUENCE: 30
LLIILRRRIR KQAHAHSK                                                    18

SEQ ID NO: 31          moltype = AA  length = 10
FEATURE                Location/Qualifiers
REGION                 1..10
                       note = peptide
source                 1..10
                       mol_type = protein
                       organism = synthetic construct
SEQUENCE: 31
RRIPNRRPRR                                                             10

SEQ ID NO: 32          moltype = AA  length = 12
FEATURE                Location/Qualifiers
REGION                 1..12
                       note = peptide
source                 1..12
                       mol_type = protein
                       organism = synthetic construct
SEQUENCE: 32
RRQRRTSKLM KR                                                          12

SEQ ID NO: 33          moltype = AA  length = 4
FEATURE                Location/Qualifiers
REGION                 1..4
                       note = peptide
source                 1..4
                       mol_type = protein
                       organism = synthetic construct
SEQUENCE: 33
GGFG                                                                    4

SEQ ID NO: 34          moltype = AA  length = 4
FEATURE                Location/Qualifiers
REGION                 1..4
                       note = peptide
source                 1..4
                       mol_type = protein
                       organism = synthetic construct
SEQUENCE: 34
RRAR                                                                    4

SEQ ID NO: 35          moltype = AA  length = 4
FEATURE                Location/Qualifiers
REGION                 1..4
                       note = peptide
source                 1..4
                       mol_type = protein
                       organism = synthetic construct
SEQUENCE: 35
GFLG                                                                    4

SEQ ID NO: 36          moltype = AA  length = 4
FEATURE                Location/Qualifiers
REGION                 1..4
                       note = peptide
source                 1..4
                       mol_type = protein
                       organism = synthetic construct
SEQUENCE: 36
ALAL                                                                    4

SEQ ID NO: 37          moltype = AA  length = 21
FEATURE                Location/Qualifiers
REGION                 1..21
                       note = peptide
source                 1..21
                       mol_type = protein
                       organism = synthetic construct
SEQUENCE: 37
MALPVTALLL PLALLLHAAR P                                                21
```

```
SEQ ID NO: 38            moltype = AA   length = 20
FEATURE                  Location/Qualifiers
REGION                   1..20
                         note = peptide
source                   1..20
                         mol_type = protein
                         organism = synthetic construct
SEQUENCE: 38
HMIGICVTLT VIIVCSVFIY                                                      20

SEQ ID NO: 39            moltype = AA   length = 21
FEATURE                  Location/Qualifiers
REGION                   1..21
                         note = peptide
source                   1..21
                         mol_type = protein
                         organism = synthetic construct
SEQUENCE: 39
LLLLFWLGWL GMLAGAVVII V                                                    21

SEQ ID NO: 40            moltype = AA   length = 24
FEATURE                  Location/Qualifiers
REGION                   1..24
                         note = peptide
source                   1..24
                         mol_type = protein
                         organism = synthetic construct
SEQUENCE: 40
ALSPVELGLL LLPFVVMLLA ALCV                                                 24

SEQ ID NO: 41            moltype = AA   length = 21
FEATURE                  Location/Qualifiers
REGION                   1..21
                         note = peptide
source                   1..21
                         mol_type = protein
                         organism = synthetic construct
SEQUENCE: 41
IMIVLVMLLN IGLAILFVHF L                                                    21

SEQ ID NO: 42            moltype = AA   length = 21
FEATURE                  Location/Qualifiers
REGION                   1..21
                         note = peptide
source                   1..21
                         mol_type = protein
                         organism = synthetic construct
SEQUENCE: 42
STVFTVLLLL LGMAAYSFGW V                                                    21

SEQ ID NO: 43            moltype = AA   length = 21
FEATURE                  Location/Qualifiers
REGION                   1..21
                         note = peptide
source                   1..21
                         mol_type = protein
                         organism = synthetic construct
SEQUENCE: 43
GLLACIAAVL MLPAFLYLHY V                                                    21

SEQ ID NO: 44            moltype = AA   length = 42
FEATURE                  Location/Qualifiers
REGION                   1..42
                         note = peptide
source                   1..42
                         mol_type = protein
                         organism = synthetic construct
SEQUENCE: 44
TYVMAAVLCQ VIIFGCMFEI VTPPIVSTGM ALLLILYLLF YM                             42

SEQ ID NO: 45            moltype = AA   length = 21
FEATURE                  Location/Qualifiers
REGION                   1..21
                         note = peptide
source                   1..21
                         mol_type = protein
                         organism = synthetic construct
SEQUENCE: 45
```

```
IGWMLSFTIS ELLFLIILAA I                                                    21

SEQ ID NO: 46            moltype = AA  length = 20
FEATURE                  Location/Qualifiers
REGION                   1..20
                         note = peptide
source                   1..20
                         mol_type = protein
                         organism = synthetic construct
SEQUENCE: 46
VGHSLSIFTL VISLGIFVFF                                                      20

SEQ ID NO: 47            moltype = AA  length = 20
FEATURE                  Location/Qualifiers
REGION                   1..20
                         note = peptide
source                   1..20
                         mol_type = protein
                         organism = synthetic construct
SEQUENCE: 47
VTLHKNMFLT YILNSMIIII                                                      20

SEQ ID NO: 48            moltype = AA  length = 23
FEATURE                  Location/Qualifiers
REGION                   1..23
                         note = peptide
source                   1..23
                         mol_type = protein
                         organism = synthetic construct
SEQUENCE: 48
ILHFFHQYMM ACNYFWMLCE GIY                                                  23

SEQ ID NO: 49            moltype = AA  length = 20
FEATURE                  Location/Qualifiers
REGION                   1..20
                         note = peptide
source                   1..20
                         mol_type = protein
                         organism = synthetic construct
SEQUENCE: 49
WYYLLGWGFP LVPTTIHAIT                                                      20

SEQ ID NO: 50            moltype = AA  length = 24
FEATURE                  Location/Qualifiers
REGION                   1..24
                         note = peptide
source                   1..24
                         mol_type = protein
                         organism = synthetic construct
SEQUENCE: 50
LLYIIHGPVM AALVVNFFFL LNIV                                                 24

SEQ ID NO: 51            moltype = AA  length = 18
FEATURE                  Location/Qualifiers
REGION                   1..18
                         note = peptide
source                   1..18
                         mol_type = protein
                         organism = synthetic construct
SEQUENCE: 51
ATMILVPLLG IQFVVFPW                                                        18

SEQ ID NO: 52            moltype = AA  length = 22
FEATURE                  Location/Qualifiers
REGION                   1..22
                         note = peptide
source                   1..22
                         mol_type = protein
                         organism = synthetic construct
SEQUENCE: 52
YVMHSLIHFQ GFFVATIYCF CN                                                   22

SEQ ID NO: 53            moltype = AA  length = 21
FEATURE                  Location/Qualifiers
REGION                   1..21
                         note = peptide
source                   1..21
                         mol_type = protein
                         organism = synthetic construct
```

```
SEQUENCE: 53
AAVFFGCTFV AFGPAFALFL I                                              21

SEQ ID NO: 54           moltype = AA  length = 21
FEATURE                 Location/Qualifiers
REGION                  1..21
                        note = peptide
source                  1..21
                        mol_type = protein
                        organism = synthetic construct
SEQUENCE: 54
VIILVAGAFF WLVSLLLASV V                                              21

SEQ ID NO: 55           moltype = AA  length = 21
FEATURE                 Location/Qualifiers
REGION                  1..21
                        note = peptide
source                  1..21
                        mol_type = protein
                        organism = synthetic construct
SEQUENCE: 55
YGLLIFGAAV SVLLQEVFRF A                                              21

SEQ ID NO: 56           moltype = AA  length = 21
FEATURE                 Location/Qualifiers
REGION                  1..21
                        note = peptide
source                  1..21
                        mol_type = protein
                        organism = synthetic construct
SEQUENCE: 56
YVSGLSFGII SGVFSVINIL A                                              21

SEQ ID NO: 57           moltype = AA  length = 21
FEATURE                 Location/Qualifiers
REGION                  1..21
                        note = peptide
source                  1..21
                        mol_type = protein
                        organism = synthetic construct
SEQUENCE: 57
TSAFLTAAII LLHTFWGVVF F                                              21

SEQ ID NO: 58           moltype = AA  length = 18
FEATURE                 Location/Qualifiers
REGION                  1..18
                        note = peptide
source                  1..18
                        mol_type = protein
                        organism = synthetic construct
SEQUENCE: 58
ATMILVPLLG IQFVVFPW                                                  18

SEQ ID NO: 59           moltype = AA  length = 21
FEATURE                 Location/Qualifiers
REGION                  1..21
                        note = peptide
source                  1..21
                        mol_type = protein
                        organism = synthetic construct
SEQUENCE: 59
LLPIYAVTVS MGLWAFITAG G                                              21

SEQ ID NO: 60           moltype = AA  length = 21
FEATURE                 Location/Qualifiers
REGION                  1..21
                        note = peptide
source                  1..21
                        mol_type = protein
                        organism = synthetic construct
SEQUENCE: 60
NIWTHLLGCV FFLCLGIFYM F                                              21

SEQ ID NO: 61           moltype = AA  length = 21
FEATURE                 Location/Qualifiers
REGION                  1..21
                        note = peptide
source                  1..21
                        mol_type = protein
```

-continued

```
                          organism = synthetic construct
SEQUENCE: 61
VVFGLFFLGA ILCLSFSWLF H                                                  21

SEQ ID NO: 62             moltype = AA   length = 21
FEATURE                   Location/Qualifiers
REGION                    1..21
                          note = peptide
source                    1..21
                          mol_type = protein
                          organism = synthetic construct
SEQUENCE: 62
LFSKLDYSGI ALLIMGSFVP W                                                  21

SEQ ID NO: 63             moltype = AA   length = 21
FEATURE                   Location/Qualifiers
REGION                    1..21
                          note = peptide
source                    1..21
                          mol_type = protein
                          organism = synthetic construct
SEQUENCE: 63
CFIYLIVICV LGIAAIIVSQ W                                                  21

SEQ ID NO: 64             moltype = AA   length = 21
FEATURE                   Location/Qualifiers
REGION                    1..21
                          note = peptide
source                    1..21
                          mol_type = protein
                          organism = synthetic construct
SEQUENCE: 64
YRGVRAGVFL GLGLSGIIPT L                                                  21

SEQ ID NO: 65             moltype = AA   length = 21
FEATURE                   Location/Qualifiers
REGION                    1..21
                          note = peptide
source                    1..21
                          mol_type = protein
                          organism = synthetic construct
SEQUENCE: 65
QIGWLMLMAS LYITGAALYA A                                                  21

SEQ ID NO: 66             moltype = AA   length = 21
FEATURE                   Location/Qualifiers
REGION                    1..21
                          note = peptide
source                    1..21
                          mol_type = protein
                          organism = synthetic construct
SEQUENCE: 66
QLFHIFVVAG AFVHFHGVSN L                                                  21

SEQ ID NO: 67             moltype = AA   length = 448
FEATURE                   Location/Qualifiers
REGION                    1..448
                          note = peptide
source                    1..448
                          mol_type = protein
                          organism = synthetic construct
SEQUENCE: 67
EVQLVESGGG LVQPGGSLRL SCAASGFTFS DSWIHWVRQA PGKGLEWVAW ISPYGGSTYY         60
ADSVKGRFTI SADTSKNTAY LQMNSLRAED TAVYYCARRH WPGGFDYWGQ GTLVTVSSAS        120
TKGPSVFPLA PSSKSTSGGT AALGCLVKDY FPEPVTVSWN SGALTSGVHT FPAVLQSSGL        180
YSLSSVVTVP SSSLGTQTYI CNVNHKPSNT KVDKKVEPKS CDKTHTCPPC PAPELLGGPS        240
VFLFPPKPKD TLMISRTPEV TCVVVDVSHE DPEVKFNWYV DGVEVHNAKT KPREEQYAST        300
YRVVSVLTVL HQDWLNGKEY KCKVSNKALP APIEKTISKA KGQPREPQVY TLPPSREEMT        360
KNQVSLTCLV KGFYPSDIAV EWESNGQPEN NYKTTPPVLD SDGSFFLYSK LTVDKSRWQQ        420
GNVFSCSVMH EALHNHYTQK SLSLSPGK                                           448

SEQ ID NO: 68             moltype = AA   length = 55
FEATURE                   Location/Qualifiers
REGION                    1..55
                          note = peptide
source                    1..55
                          mol_type = protein
                          organism = synthetic construct
SEQUENCE: 68
```

FVPVFLPAKP TTTPAPRPPT PAPTIASQPL SLRPEACRPA AGGAVHTRGL DFACD        55

```
SEQ ID NO: 69           moltype = AA   length = 5
FEATURE                 Location/Qualifiers
REGION                  1..5
                        note = peptide
source                  1..5
                        mol_type = protein
                        organism = synthetic construct
SEQUENCE: 69
GGGGS                                                                5

SEQ ID NO: 70           moltype = AA   length = 5
FEATURE                 Location/Qualifiers
REGION                  1..5
                        note = peptide
source                  1..5
                        mol_type = protein
                        organism = synthetic construct
SEQUENCE: 70
GGGSS                                                                5

SEQ ID NO: 71           moltype = AA   length = 5
FEATURE                 Location/Qualifiers
REGION                  1..5
                        note = peptide
source                  1..5
                        mol_type = protein
                        organism = synthetic construct
SEQUENCE: 71
GGGSG                                                                5

SEQ ID NO: 72           moltype = AA   length = 10
FEATURE                 Location/Qualifiers
REGION                  1..10
                        note = peptide
source                  1..10
                        mol_type = protein
                        organism = synthetic construct
SEQUENCE: 72
GGGGSGGGGS                                                          10

SEQ ID NO: 73           moltype = AA   length = 6
FEATURE                 Location/Qualifiers
REGION                  1..6
                        note = peptide
source                  1..6
                        mol_type = protein
                        organism = synthetic construct
SEQUENCE: 73
HHHHHH                                                               6

SEQ ID NO: 74           moltype = AA   length = 8
FEATURE                 Location/Qualifiers
REGION                  1..8
                        note = peptide
source                  1..8
                        mol_type = protein
                        organism = synthetic construct
SEQUENCE: 74
HHHHHHHH                                                             8

SEQ ID NO: 75           moltype = AA   length = 10
FEATURE                 Location/Qualifiers
REGION                  1..10
                        note = peptide
source                  1..10
                        mol_type = protein
                        organism = synthetic construct
SEQUENCE: 75
HHHHHHHHHH                                                          10

SEQ ID NO: 76           moltype = AA   length = 218
FEATURE                 Location/Qualifiers
REGION                  1..218
                        note = peptide
source                  1..218
                        mol_type = protein
                        organism = synthetic construct
```

```
SEQUENCE: 76
MSPILGYWKI KGLVQPTRLL LEYLEEKYEE HLYERDEGDK WRNKKFELGL EFPNLPYYID    60
GDVKLTQSMA IIRYIADKHN MLGGCPKERA EISMLEGAVL DIRYGVSRIA YSKDFETLKV   120
DFLSKLPEML KMFEDRLCHK TYLNGDHVTH PDFMLYDALD VVLYMDPMCL DAFPKLVCFK   180
KRIEAIPQID KYLKSSKYIA WPLQGWQATF GGGDHPPK                          218

SEQ ID NO: 77          moltype = AA   length = 396
FEATURE                Location/Qualifiers
REGION                 1..396
                       note = peptide
source                 1..396
                       mol_type = protein
                       organism = synthetic construct
SEQUENCE: 77
MKIKTGARIL ALSALTTMMF SASALAKIEE GKLVIWINGD KGYNGLAEVG KKFEKDTGIK    60
VTVEHPDKLE EKFPQVAATG DGPDIIFWAH DRFGGYAQSG LLAEITPDKA FQDKLYPFTW   120
DAVRYNGKLI AYPIAVEALS LIYNKDLLPN PPKTWEEIPA LDKELKAKGK SALMFNLQEP   180
YFTWPLIAAD GGYAFKYENG KYDIKDVGVD NAGAKAGLTF LVDLIKNKHM NADTDYSIAE   240
AAFNKGETAM TINGPWAWSN IDTSKVNYGV TVLPTFKGQP SKPFVGVLSA GINAASPNKE   300
LAKEFLENYL LTDEGLEAVN KDKPLGAVAL KSYEEELAKD PRIAATMENA QKGEIMPNIP   360
QMSAFWYAVR TAVINAASGR QTVDEALKDA QTRITK                            396

SEQ ID NO: 78          moltype = AA   length = 8
FEATURE                Location/Qualifiers
REGION                 1..8
                       note = peptide
source                 1..8
                       mol_type = protein
                       organism = synthetic construct
SEQUENCE: 78
WSHPQFEK                                                             8

SEQ ID NO: 79          moltype = AA   length = 15
FEATURE                Location/Qualifiers
REGION                 1..15
                       note = peptide
source                 1..15
                       mol_type = protein
                       organism = synthetic construct
SEQUENCE: 79
GGGGSGGGGS GGGGS                                                    15
```

COMPOSITION AND METHOD OF USE RECOMBINANT FUSION PROTEIN TO GENERATE CAR-IMMUNE CELLS

CROSS REFERENCE TO RELATED APPLICATION

The present application claims priority to U.S. Patent Application 63/320,885 filed Mar. 17, 2022, the entire contents of which is incorporated herein for all purposes by this reference.

REFERENCE TO SEQUENCE LISTING

The Sequence Listing submitted as a XML file named "A286129_Sequence listing as filed," created on Mar. 16, 2023, and having a size of 98.5 KB is hereby incorporated by reference.

FIELD

Provided herein are a recombinant chimeric antigen receptor (CAR) fusion protein, a method of modifying an immune cell into a CAR immune cell by treating the immune cell with the recombinant CAR fusion protein, and a method of treating cancer by administering the CAR immune cell to a subject in need thereof.

BACKGROUND

Chimeric antigen receptor (CAR) technology has developed to modify immune cells into cancer-specifically stimulated immune cells. CAR-T or CAR-NK cells are widely evaluated in various clinical trials and few of them are being prescribed in clinics. A CAR is composed of an extracellular scFv domain for cancer targeting, intracellular co-stimulatory domains, and transmembrane domains. CAR-immune cells can recognize cancer cells through the binding of the extracellular scFv antibody to the target antigen on cancer cells, which in turn leads to the stimulation of the immune cells to exert stronger anti-cancer activity. The conventional CAR technology raises limitations in its use due to the use of viral vectors for CAR-gene transfer, lengthy generation time that makes it not a feasible option for patients who need immediate treatment, and more importantly, the need for isolation, modification, expansion ex vivo prior to infusion back to the patient.

SUMMARY

To overcome the above limitations, the present disclosure provides a novel recombinant CAR fusion protein capable of modifying immune cells into CAR-immune cells without the need for genetic modifications.

In particular, disclosed is a recombinant chimeric antigen receptor (CAR) fusion protein comprising, in order, an immune cell targeting domain, a cleavable peptide, a membrane targeting domain, an extracellular cancer targeting domain, a transmembrane domain, and an intracellular signaling domain. In one embodiment, the immune cell targeting domain is a NK cell targeting domain, or a T cell targeting domain. In another embodiment, the NK cell targeting domain is a NK cell-targeting-scFv antibody, -full antibody, -minibody, -Fab, or a peptide comprising an anti-NKp46 VH, IgG hinge, IgG CH2 and IgG CH3. In one embodiment, the cleavable peptide is a peptide which is configured to be enzymatically cleaved. In one embodiment, the membrane targeting domain is a peptide from interleukin-1 receptor type 1, 4F2 cell-surface antigen heavy chain, a linker for activation of T-cells family member 1, junctophilin-1, antilisterial bacteriocin subtilosin biosynthesis protein AlbG, calcitonin receptor, gamma-secretase subunit APH-1A, or adipnectin receptor protein 2. In one embodiment, the extracellular cancer targeting domain is an anti-PD-L1 Vh, anti-HER2, ani-HER3, anti-TROP2, or any other cancer specific-antigen targeting antibody. In another embodiment, the recombinant CAR fusion protein further comprises a hinge region between the extracellular cancer targeting domain and the transmembrane domain. In one embodiment, the transmembrane domain is NKG2D. In another embodiment, the intracellular signaling domain comprises a CD3 zeta (CD3ζ) signaling domain and a co-stimulatory signaling region selected from the group consisting of 2B4, DAP12, GITR, CD137, OX40. In one embodiment, the recombinant CAR fusion protein further comprises a tag sequence. In another embodiment, the tag sequence is selected from the group consisting of a histidine tag, glutathione-S-transferase tag, or hemagglutinin tag.

The present disclosure also provides a method of modifying an immune cell into a chimeric antigen receptor (CAR) immune cell, comprising treating the immune cell with the recombinant CAR fusion protein discussed above. In one embodiment, the CAR fusion protein is in a concentration of about 1,000 nM to about 2,000 nM.

The present disclosure also provides a method of treating cancer comprising administering a CAR immune cell, which has been prepared by treating an immune cell with the a recombinant CAR fusion protein, to a subject in need thereof.

The present disclosure further provides a method of treating cancer comprising administering the recombinant CAR fusion protein discussed above to a subject in need thereof. In one embodiment, the CAR fusion protein is in a concentration of about 1,000 nM to about 2,000 nM.

The present disclosure also provides a method of treating cancer comprising administering to a subject in need thereof: (i) a recombinant chimeric antigen receptor (CAR) fusion protein comprising, in order: an immune cell targeting domain, a cleavable peptide, a membrane targeting domain, an extracellular cancer targeting domain, a transmembrane domain, and an intracellular signaling domain; and (ii) a CAR immune cell. In one embodiment, the CAR immune cell is prepared by treating an immune cell with the recombinant CAR fusion protein.

Additional embodiments are described herein.

BRIEF DESCRIPTION OF THE DRAWINGS

FIG. 1 shows the amino acid sequence of the recombinant CAR fusion protein against anti-PD-L1.

FIGS. 8A-1, 8A-2 and 8B show data comparing the anti-cancer activity of the NK cells and the CAR-NK cells.

FIGS. 10A, 10B-1, 10B-2 and 10C show data relating to in vivo CAR-NK retention in vitro.

DEFINITIONS

Figure 2:
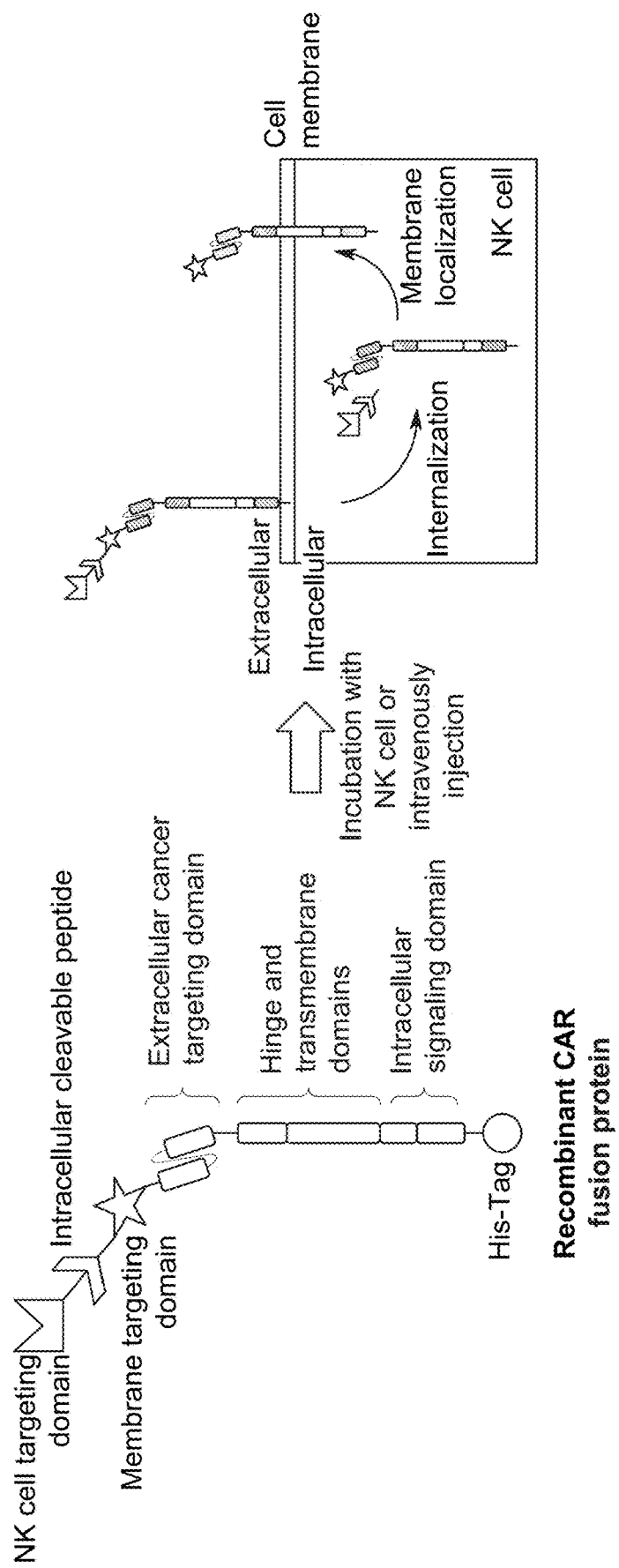
FIG. 2 shows the structure of the recombinant CAR fusion protein of the present disclosure and describes how it modifies immune cells to chimeric antigen receptor (CAR) immune cells.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide" is a reference to one or more peptides and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition. For example, "treating" cancer may refer to inhibiting growth and/or spread of the cancer cells, killing the cancer cells, or shrinking the cancer cells. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-$\beta$, and/or reorganization of cytoskeletal structures, and the like.

A "stimulatory molecule," as the term is used herein, means a molecule on a T cell or NK cell that specifically binds with a cognate stimulatory ligand present on an antigen presenting cell.

A "stimulatory ligand," as used herein, means a ligand that when present on an antigen presenting cell (e.g., an APC, a dendritic cell, a B-cell, and the like) can specifically bind with a cognate binding partner (referred to herein as a "stimulatory molecule") on a T cell or NK cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, a superagonist anti-CD2 antibody and the like.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to kidney cancer, spleen cancer, lung cancer, liver cancer, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "therapeutically effective amount" means an amount of a therapeutic, prophylactic, and/or diagnostic agent (e.g., CAR) that is sufficient, when administered to a subject suffering from or susceptible to a disease, disorder, and/or condition, to treat, alleviate, ameliorate, relieve, alleviate symptoms of, prevent, delay onset of, inhibit progression of, reduce severity of, and/or reduce incidence of the disease, disorder, and/or condition.

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human.

DETAILED DESCRIPTION

1. The Recombinant Chimeric Antigen Receptor (CAR) Fusion Protein

The present disclosure provides a recombinant chimeric antigen receptor (CAR) fusion protein comprising, in order, an immune cell targeting domain, a cleavable peptide, a membrane targeting domain, an extracellular cancer targeting domain, a transmembrane domain, and an intracellular signaling domain. The structure of an exemplary embodiment of the recombinant CAR fusion protein of the present disclosure is described in FIG. 2. In this embodiment, the recombinant CAR fusion protein was designed to modify NK cells into CAR NK cells via in vivo application. As described in FIG. 2, the recombinant CAR fusion protein can target NK cells by the NK cell targeting domain (i.e., the immune cell targeting domain), and enter into NK cell's cytoplasm by antigen-antibody binding. Once the recombinant CAR fusion protein is entered into the cytoplasm, the recombinant CAR fusion protein is separated into the NK cell targeting domain and the rest of the recombinant CAR fusion protein domains because of the cleavable peptide (which is enzymatically cleaved). Then, the membrane targeting domain induces the rest of the recombinant CAR fusion protein domains (i.e., the membrane targeting domain, extracellular cancer targeting domain, transmembrane domain, and intracellular signaling domain; also referred to the CAR domain) locate in the cell membrane. Therefore, the CAR domain can increase anti-cancer activity of the NK cells upon binding with cancer cells.

The recombinant CAR fusion protein of the present disclosure has advantages over the conventional CAR technology as it can generate CAR-immune cells without viral vector, within a day, and either ex vivo or in vivo. More importantly, this technology allows a cell-free immunotherapy, which is safer and less expensive than the conventional CAR-immune cells.

The Immune Cell Targeting Domain

In one embodiment, the immune cell targeting domain identifies the target immune cell, and thus the recombinant CAR fusion protein enters into the target immune cell through antigen-antibody binding. The immune cell targeting domain is selected from the group consisting of a NK cell targeting domain, a T cell targeting domain, a dendritic cell targeting domain, and a macrophage targeting domain.

For instance, the NK cell targeting domain may be included in the recombinant CAR fusion protein such that the recombinant CAR fusion protein identifies and enters into NK cells. The NK cell targeting domain may be an antibody, antibody fragment or an antigen-binding fragment targeting NK cells. For instance, the NK cell targeting domain may be a NK cell-targeting antibody, NK cell-targeting-scFv antibody, a peptide comprising a NK cell-targeting antibody-VH, IgG hinge, IgG CH2 and IgG CH3. The NK cell targeting antibody can be anti-NKp46, anti-NKp30, anti-NKp44, anti-NKp80, anti-NKG2A, anti-NKG2C, anti-NKG2D, anti-CD16, anti-CD56, anti-KIR-s, or anti-CD122.

In addition, the T cell targeting domain may be included in the recombinant CAR fusion protein so that the recombinant CAR fusion protein identifies and enters into T cells. For instance, the T cell targeting domain may be a T cell-targeting antibody, Tcell-targeting-scFv antibody, a peptide comprising a T cell-targeting antibody-VH, IgG hinge, IgG CH2 and IgG CH3. The T cell targeting antibody can be anti-CD3, anti-CD8, anti-CD45R, anti-NKp46, anti-NKp30, anti-TIM3, anti-TIGIT, anti-LAG3, or anti-CTLA4.

In another embodiment, when the recombinant CAR fusion protein is used to modify an immune cell into a chimeric antigen receptor (CAR) immune cell in ex vivo application, since specific immune cells may be directly treated with the recombinant CAR fusion protein, the immune cell targeting domain may be also selected from any protein-transduction domain, which is not specific to the target immune cell, but allows non-specific transduction of the recombinant CAR fusion protein, into any cells. In one embodiment, the immune cell targeting domain for ex vivo application (which is not specific to certain immune cells) may include Tat or a Tat peptide, poly-arginine, antennapedia (Antp) or Antp peptide, penetratin, SAP, PTD-5, K-FGF (SN50 peptide), HIV-1 Rev, FHV, HTLV-II, NLS, transportan, pVEC. Examples of these domains can be, but are not limited to Tat (YGRKKRRQRRR; SEQ ID NO: 2) or a Tat peptide (RKKRRQRRR; SEQ ID NO: 3), poly-arginine (RRRRRR; SEQ ID NO: 4; RRRRRRRR; SEQ ID NO: 5; RRRRRRRRR; SEQ ID NO: 6), antennapedia (Antp) or Antp peptide (RQIKIWFQNRRMKW; SEQ ID NO: 7), penetratin (RQIKIWFQNRRMKWKK; SEQ ID NO: 8), SAP (VRLPPPVRLPPPVRLPPP; SEQ ID NO: 9), PTD-5 (RRQRRTSKLMKR; SEQ ID NO: 10), K-FGF (SN50 peptide) (AAVALLPAVLLALLAP; SEQ ID NO: 11), HIV-1 Rev (TRQARRNRRRRWRERQR; SEQ ID NO: 12), FHV (RRRRNRTRRNRRRVR; SEQ ID NO: 13), HTLV-II (TRRQRTRRATTNR; SEQ ID NO: 14), NLS (KRPAAIK-KAGQAKKKK; SEQ ID NO: 15), transportan (GWTLN-SAGYLLGKINLKALAALAKKIL; SEQ ID NO: 16), pVEC (LLIILRRRIRKQAHAHSK; SEQ ID NO: 17). See also Table 1 below.

TABLE 1

| Name | Sequence |
| --- | --- |
| Tat 47-60 | YGRKKRRQRRRPPQ (SEQ ID NO: 18) |
| Penetratin | RQIKIWFQNRRMKWKK (SEQ ID NO: 19) |

TABLE 1-continued

| Name | Sequence |
| --- | --- |
| Transportan [1] | GWTLNSAGYLLGKINLKALAALAKKL (SEQ ID NO: 20) |
| Xentry, N-terminal region of the X-protein of the hepatitis B virus | LCLRPVG (SEQ ID NO: 21) |
| Poly Arginine$_{8-10}$ | RRRRRRRR(RR) (SEQ ID NO: 22) |
| Lysine$_{8-10}$ [2] | KKKKKKKK(KK) (SEQ ID NO: 23) |
| MAP [3] | KLALKLALKALKAALKLA SEQ ID NO: 24) |
| Pep-1 [4] | KETWWETWWTEWSQPKKKRKV (SEQ ID NO: 25) |
| Pept1 [5] | PLILLRLLRGQF (SEQ ID NO: 26) |
| Pept2 [5] | PLIYLRLLRGQF (SEQ ID NO: 27) |
| IVV-14 [6] | KLWMRWYSPTTRRYG (SEQ ID NO: 28) |
| Amphiphilic model peptide [7] | KLALKLALKALKAALKLA (SEQ ID NO: 29) |
| pVEC [8] | LLIILRRRIRKQAHAHSK (SEQ ID NO: 30) |
| HRSV [9] | RRIPNRRPRR (SEQ ID NO: 31) |
| PTD-5 [10] | RRQRRTSKLMKR (SEQ ID NO: 32) |

[1] Pooga et al., *FASEB J.* 12: 67-77 (1998)
[2] Mi et al., *J. Biol. Chem.* 277(33): 30208-30218 (2002)
[3] Robbins et al., *Cancer Res.* 51: 3657-3662 (1991)
[4] Deshayes et al., *Biochemistry* 43(6): 1449-1457 (2004)
[5] Marks et al., *J. Am. Chem. Soc.* 133(23): 8995-9004 (2011)
[6] Kamide et al., *Int. J. Mol. Med.* 25(1): 41-51 (2010)
[7] Lindgren et al. *Trend Pharmacol. Sci.* 21(3): 99-103 (2000)
[8] Sidhu and Weiss, in *Anticancer Drug Development*, Baguley and Kerr, Ed., Academic Press 237-248 (2002)
[9] Langedijk et al, in *Drug Transport(ers) and the Diseased Brain*, International Congress Series, Elsevier 95-107 (2005)
[10] Mi et al., *Mol. Ther.* 2(4): 339-347 (2000)

The Cleavable Peptide

In one embodiment, the cleavable peptide is enzymatically cleaved to separate the immune cell targeting domain from the rest of the recombinant CAR fusion protein domains once the recombinant CAR fusion protein enters into the immune cell.

The cleavable peptide may be protease cleavage site: Gly-Gly-Phe-Gly (GGFG; SEQ ID NO: 33), Furin cleavage site (RRAR; SEQ ID NO: 34), Capthesin cleavage site (Phe-Lys (FK), Ala-Ala-Asn (AAN), Gly-Phe-Leu-Gly (GFLG; SEQ ID NO: 35)), or Legumain cleavage site (Ala-Leu-Ala-Leu (ALAL; SEQ ID NO: 36)).

The Membrane Targeting Domain

In one embodiment, once the immune cell targeting domain is separated from the rest of the recombinant CAR fusion protein domains by the cleavable peptide is enzymatically cleaved, the membrane targeting domain induces the rest of the recombinant CAR fusion protein domains to locate in cell membrane (triggers exocytosis of the rest of the recombinant CAR fusion protein domains toward the outer cell membrane).

The membrane targeting domain may be a peptide from T-cell surface glycoprotein CD8 alpha chain (MALPVTALLLPLALLLHAARP; SEQ ID NO: 37), interleukin-1 receptor type 1, 4F2 cell-surface antigen heavy chain, linker for activation of T-cells family member 1, junctophilin-1, antilisterial bacteriocin subtilosin biosynthesis protein AlbG, calcitonin receptor, gamma-secretase subunit APH-1A, adipnectin receptor protein 2. Examples of these peptides can be, but are not limited to, interleukin-1 receptor type 1 (HMIGICVTLTVIIVCSVFIY; SEQ ID NO: 38), 4F2 cell-surface antigen heavy chain (LLLLFWLGWLGMLAGAVVIIV; SEQ ID NO: 39), linker for activation of T-cells family member 1 (ALSPVELGLLLLPFVVMLLAALCV; SEQ ID NO: 40), junctophilin-1 (IMIVLVMLLNIGLAILFVHFL; SEQ ID NO: 41), antilisterial bacteriocin subtilosin biosynthesis protein AlbG (STVFTVLLLLLGMAAYSFGWV-SEQ ID NO: 42; GLLACIAAVLMLPAFLYLHYV-SEQ ID NO: 43; TYVMAAVLCQVIIFGCMFEIV; TPPIVSTGMALLLILYLLFYM-SEQ ID NO: 44; IGWMLSFTISELLFLIILAAI-SEQ ID NO: 45), calcitonin receptor (VGHSLSIFTLVISLGIFVFF-SEQ ID NO: 46; VTLHKNMFLTYILNSMIIII-SEQ ID NO: 47; ILHFFHQYMMACNYFWMLCEGIY-SEQ ID NO: 48; WYYLLGWGFPLVPTTIHAIT-SEQ ID NO: 49; LLYIIHGPVMAALVVNFFFLLNIV-SEQ ID NO: 50; ATMILVPLLGIQFVVFPW-SEQ ID NO: 51; YVMHSLIHFQGFFVATIYCFCN-SEQ ID NO: 52), gamma-secretase subunit APH-1A (AAVFFGCTFVAFGPAFALFLI-SEQ ID NO: 53; VIILVAGAFFWLVSLLLASVV-SEQ ID NO: 54; YGLLIFGAAVSVLLQEVFRFA-SEQ ID NO: 55; YVSGLSFGIISGVFSVINILA-SEQ ID NO: 56; TSAFLTAAIILLHTFWGVVFF-SEQ ID NO: 57; ATMILVPLLGIQFVVFPW-SEQ ID NO: 58; LLPIYAVTVSMGLWAFITAGG-SEQ ID NO: 59), or adipnectin receptor protein 2 (NIWTHLLGCVFFLCLGIFYMF-SEQ ID NO: 60; VVFGLFFLGAILCLSFSWLFH-SEQ ID NO: 61; LFSKLDYSGIALLIMGSFVPW-SEQ ID NO: 62; CFIYLIVICVLGIAAIIVSQW-SEQ ID NO: 63; YRGVRAGVFLGLGLSGIIPTL-SEQ ID NO: 64; QIGWLMLMASLYITGAALYAA-SEQ ID NO: 65; QLFHIFVVAGAFVHFHGVSNL-SEQ ID NO: 66).

The Extracellular Cancer Targeting Domain

In one embodiment, the extracellular cancer targeting domain identifies and binds to an antigen on cancer cells once the immune cells are modified into chimeric antigen receptor (CAR) immune cells by the recombinant CAR fusion protein.

The extracellular cancer targeting domain can be an antibody, an antibody fragment or an antigen-binding fragment. In one embodiment, the extracellular cancer targeting domain may be PD-L1 antigen binding domain, anti-PD-L1 Vh (EVQLVESGGGLVQPGGSLRLSCAASGFTFSDSWIHWVRQAPGKGLEWVAWISPYG GSTYYADSVKGRFTISADTSKNTAYLQMNSLRAEDTAVYYCARRHWPGGFDYWGQ GTLVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVD KKVEPKSCDKT HTCPPCPAPELLGGPSVFLFPPKPKDTLMISRTPEVTCVVVDVSHEDPEVKFNWYVD GVEVHNAKTKPREEQYASTYRVVSVLTVLHQDWLNGKEYKCKVSNKALPAPIEKTI SKAKGQPREPQVYTLPPSREEMTKNQVSLTCLVKGFYPSDIAVEWESNGQPENNYKT TPPVLDSDGSFFLYSKLTVDKSRWQQ GNVFSCSVMHEALHNHYTQKSLSLSPGK; SEQ ID NO: 67), a HER2, CD19, CD33, CD20, CD30, CD138, CD123, CD79b, CD37, FOLR1, TROP2, DLL3, ENPP3, CA6, B cell maturation antigen (BCMA), carbonic anhydrase IX (CAIX), CD171, carcinoembryonic antigen (CEA), ERBB2, EGFR, EGFRvIII, GD2, αFR, GP100, Lewis Y, melanoma antigen recognized by T cells 1 (MART 1), melanoma antigen A3 (MAGEA3), NYSEO1, P53, prostate specific membrane antigen (PSMA), mucin 16 (MUC16), glypican 3 (GPC3), mesothelin antigen binding domain.

The Hinge Region

In one embodiment, the recombinant CAR fusion protein further comprises a hinge region. In some aspects, the hinge region can be located between the extracellular cancer targeting domain and the transmembrane domain. The hinge region may increase the distance of the extracellular cancer targeting domain and the transmembrane domain, and provide flexibility. In one embodiment, the hinge region may contain 12-45 amino acids. For instance, the hinge region may be CD8 hinge (FVPVFLPAKPTTTPAPRPPTPAPTIASQPLSLRPEACRPAAGGAVHTRGLDFACD; SEQ ID NO: 68), CD28, IgG1, and IgG4.

The Transmembrane Domain

In one embodiment, during the process of exocytosis of the rest of the recombinant CAR fusion protein domains toward the outer cell membrane, the transmembrane domain is positioned in the cell membrane, and thus the intracellular signaling domain is positioned beneath the inner cell membrane.

In some aspects, the transmembrane domain can be NKG2D, an immunoglobulin Fc domain, a CD8α domain, CD3ζ, FcεR1γ, CD4, CD7, CD28, OX40, H2-Kb, ICOS, NKG2D, NKp44, and CD16.

The Intracellular Signaling Domain

In one embodiment, the intracellular signaling domain comprises a CD3 zeta (CD3ζ) signaling domain, and a co-stimulatory signaling region selected from the group consisting of 2B4, DAP12, GITR, CD137, OX40, CD27, ICOS, CD40, 41BB, and DAP10.

The Tag Sequence

In one embodiment, the recombinant CAR fusion protein further comprises a tag sequence. In some aspects, the tag sequence can be located at the C-terminal or N-terminal end of the recombinant CAR fusion protein, optionally via a linker. The linker may be a serine-glycine linker such as GGGGS (SEQ ID NO: 69), GGGSS (SEQ ID NO: 70), GGGSG (SEQ ID NO: 71), or multiple variants thereof such as GGGGSGGGGS (SEQ ID NO: 72) or (GGGGS-SEQ ID NO: 69)m, (GGGSS-SEQ ID NO: 70)m, (GGGSG-SEQ ID NO: 71)m, where m is an integer from 1 to 5, from 1 to 4 or from 1 to 3. In a preferred embodiment m is 2.

In some aspects, the tag sequence can be, but is not limited to, a histidine tag, glutathione-S-transferase tag, maltose binding protein tag, Strep tag, or hemagglutinin tag. Examples of these tags can be, but are not limited to histidine tag (HHHHHH-SEQ ID NO: 73; HHHHHHHH-SEQ ID NO: 74; HHHHHHHHHH-SEQ ID NO: 75), glutathione-S-transferase tag (MSPILGYWKIKGLVQPTRLLLEYLEEKYEEHLYERDEGDK WRNKKFELGLEFPNLPYYIDGDVKLTQS-MAIIRYIADKHNMLGGCPKERAEISMLEG AVLDIRYGVSRIAYSKDFETLKVDFLSKLPEMLKM-FEDRLCHKTYLNGDHVTHPDF MLYDALD VVLYMDPMCL DAFPKLVCFKKRIEAIPQID KYLKSSKYIAWPLQGWQATF GGGDHPPK; SEQ ID NO: 76), maltose binding protein tag (MKIKTGARILALSALTTMMFSASALAKIEEGKLVIWINGDKGYNGLAEVGKKFEKD TGIKVTVEHPDKLEEKFPQVAATGDGP- DIIFWAHDRFGGYAQSGLLAEITPDKAFQD
KLYPFTWDAVRYNGKLIAYPI-
AVEALSLIYNKDLLPNPPKTWEEIPALDKELKAKGK
SALMFNLQEPYFTWPLIAADGGYAFKYENG-
KYDIKDVGVDNAGAKAGLTFLVDLIK NKHM-
NADTDYSIAEAAFNKGETAMTINGP-
WAWSNIDTSKVNYGVTVLPTFKGQPSK
PFVGVLSAGINAASPNKELAKEFLENYLLTDE-
GLEAVNKDKPLGAVALKSYEEELAK DPRIAAT-
MENAQKGEIMPNIPQMSAFWYAVRTAVINAAS-
GRQTVDEALKDAQTRIT K; SEQ ID NO: 77), or Strep tag (WSHPQFEK; SEQ ID NO: 78).

The tag sequence can be utilized to isolate recombinant CAR protein from *E. coli* or other cells during the protein production and to verify presence of recombinant CAR protein in NK cells.

The Linker

In one embodiment, the linker may be also included between the immune cell targeting domain and the cleavable peptide. For instance, the linker may be a serine-glycine linker such as GGGGSGGGGSGGGGS (SEQ ID NO: 79), GGGGS (SEQ ID NO: 69), GGGSS (SEQ ID NO: 70), GGGSG (SEQ ID NO: 71), or multiple variants thereof such as GGGGSGGGGS (SEQ ID NO: 72) or (GGGGS-(SEQ ID NO: 69))m, (GGGSS-(SEQ ID NO: 70))m, (GGGSG-(SEQ ID NO: 71))m, where m is an integer from 1 to 5, from 1 to 4 or from 1 to 3. In a preferred embodiment m is 2.

2. The Method of Modifying an Immune Cell into a Chimeric Antigen Receptor (CAR) Immune Cell The present disclosure also provides a method of modifying an immune cell into a chimeric antigen receptor (CAR) immune cell, comprising treating the immune cell with the recombinant CAR fusion protein discussed above.

In one embodiment, the above method may be applied in both in vivo, and ex vivo.

In the in vivo application, the immune cell targeting domain may be an antibody, antibody fragment or an antigen-binding fragment targeting a specific immune cell which is to be modified into a CAR immune cell. For instance, in order to modify NK cells into CAR NK cells in the in vivo application, the immune cell targeting domain may be a NK cell targeting domain. In addition, in order to modify T cells into CAR T cells in the in vivo application, the immune cell targeting domain may be a T cell targeting domain.

The NK cell targeting domain may be an antibody, antibody fragment or an antigen-binding fragment targeting NK cells. For instance, the NK cell targeting domain may be a NK cell-targeting antibody, NK cell-targeting-scFv antibody, a peptide comprising a NK cell-targeting antibody-VH, IgG hinge, IgG CH2 and IgG CH3. The NK cell targeting antibody can be anti-NKp46, anti-NKp30, anti-NKp44, anti-NKp80, anti-NKG2A, anti-NKG2C, anti-NKG2D, anti-CD16, anti-CD56, anti-KIR-s, or and anti-CD122.

In addition, the T cell targeting domain may be a T cell-targeting antibody, Tcell-targeting-scFv antibody, a peptide comprising a T cell-targeting antibody-VH, IgG hinge, IgG CH2 and IgG CH3. The T cell targeting antibody can be anti-CD3, anti-CD8, anti-CD45R, anti-NKp46, anti-NKp30, anti-TIM3, anti-TIGIT, anti-LAG3, or anti-CTLA4.

In the ex vivo application, since specific immune cells (which are to be modified into CAR immune cells) may be directly treated with the recombinant CAR fusion protein, the immune cell targeting domain may be also selected from any protein-transduction domain, which is not specific to the target immune cell, but allows non-specific transduction of the recombinant CAR fusion protein, into any cells. In one embodiment, the immune cell targeting domain for ex vivo application (which is not specific to certain immune cells) may include Tat or a Tat peptide, poly-arginine, antennapedia (Antp) or Antp peptide, penetratin, SAP, PTD-5, K-FGF (SN50 peptide), HIV-1 Rev, FHV, HTLV-II, NLS, transportan, pVEC. Examples of these domains can be, but are not limited to Tat (YGRKKRRQRRR; SEQ ID NO: 2) or a Tat peptide (RKKRRQRRR; SEQ ID NO: 3), poly-arginine (RRRRRR; SEQ ID NO: 4; RRRRRRRR; SEQ ID NO: 5; RRRRRRRRR; SEQ ID NO: 6), antennapedia (Antp) or Antp peptide (RQIKIWFQNRRMKW; SEQ ID NO: 7), penetratin (RQIKIWFQNRRMKWKK; SEQ ID NO: 8), SAP (VRLPPPVRLPPPVRLPPP; SEQ ID NO: 9), PTD-5 (RRQRRTSKLMKR; SEQ ID NO: 10), K-FGF (SN50 peptide) (AAVALLPAVLLALLAP; SEQ ID NO: 11), HIV-1 Rev (TRQARRNRRRRWRERQR; SEQ ID NO: 12), FHV (RRRRNRTRRNRRRVR; SEQ ID NO: 13), HTLV-II (TRRQRTRRATTNR; SEQ ID NO: 14), NLS (KRPAAIK-KAGQAKKKK; SEQ ID NO: 15), transportan (GWTLN-SAGYLLGKINLKALAALAKKIL; SEQ ID NO: 16), pVEC (LLIILRRRIRKQAHAHSK; SEQ ID NO: 17). See also Table 1 above.

In one embodiment, the recombinant CAR fusion protein may be treated to immune cells at a concentration which is efficient to modify the immune cells into CAR immune cells in view of the uptake efficiency of the immune cells. For instance, the lower limit of such a concentration may be a concentration which is sufficient for the modified CAR immune cells to show a therapeutic effect for cancer. In addition, the upper limit of such a concentration may be a concentration where the uptake of the recombinant CAR fusion protein by immune cells are saturated. For instance, the recombinant Car fusion protein may be in a concentration of 1,000 nM to 2,000 nM. In another embodiment, the recombinant Car fusion protein may be in a concentration of about 1,000 nM to about 2,000 nM. In another embodiment, the lower limit may be about 1,100 nM, about 1,200 nM, about 1,300 nM, about 1,400 nM, or about 1,500 nM. In another embodiment, the upper limit may be about 1,900 nM, about 1,800 nM, about 1,700 nM, or about 1,600 nM. In another embodiment, the recombinant Car fusion protein may be in a concentration of about 1,000 nM.

3. The Method of Treating Cancer by Administering the CAR Immune Cell to a Subject in Need Thereof The present disclosure also provides a method of treating cancer comprising administering a CAR immune cell, which was prepared by treating an immune cell with the recombinant CAR fusion protein of the present disclosure, to a subject in need thereof.

In one embodiment, the CAR immune cell is prepared by the ex vivo application discussed in the present disclosure, and is administered to the subject for treating cancer.

In one embodiment, the cancer being treated can be kidney cancer, spleen cancer, lung cancer, liver cancer, breast cancer, lung cancer, B cell cancer, prostate cancer, lymphoma, Chronic lymphocytic leukemia (CLL), B cell acute lymphocytic leukemia (B-ALL), Non-Hodgkin's lymphoma (NHL), Acute lymphoblastic leukemia (ALL), myeloid malignancies, multiple myeloma, renal cell carcinoma (RCC), EGFR-positive solid tumors, Glioblastoma, neuroblastoma, Ewing's sarcoma, Osteosarcoma, acute myeloid leukemia (AML), melanoma, oesophageal, Synovial sarcoma, sarcoma, colorectal cancer, hepatocellular carcinoma, non-small cell lung cancer, pancreatic carcinoma, triple-negative invasive breast cancer, ovarian cancer, or mesothelioma.

In another embodiment, the CAR immune cell is administered to the subject in an amount which is therapeutically effective to treat cancer.

In another embodiment, the above method may further include administering a therapeutic agent. For instance, the therapeutic agent may be chemotherapy, proteasome inhibitors, immunomodulatory agents, histone deacetylase inhibitors, monoclonal antibodies, bispecific antibodies, recombinant antibodies, or immune checkpoint inhibitors.

The CAR immune cell can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a cancer, such as a blood cancer or a solid tumor.

4. The Method of Treating Cancer by Administering the Recombinant CAR Fusion Protein to a Subject in Need Thereof The present disclosure also provides a method of treating cancer comprising administering the recombinant CAR fusion protein to a subject in need thereof.

In one embodiment, the cancer being treated can be kidney cancer, spleen cancer, lung cancer, liver cancer, breast cancer, lung cancer, B cell cancer, prostate cancer, lymphoma, Chronic lymphocytic leukemia (CLL), B cell acute lymphocytic leukemia (B-ALL), Non-Hodgkin's lymphoma (NHL), Acute lymphoblastic leukemia (ALL), myeloid malignancies, multiple myeloma, renal cell carcinoma (RCC), EGFR-positive solid tumors, Glioblastoma, neuroblastoma, Ewing's sarcoma, Osteosarcoma, acute myeloid leukemia (AML), melanoma, oesophageal, Synovial sarcoma, sarcoma, colorectal cancer, hepatocellular carcinoma, non-small cell lung cancer, pancreatic carcinoma, triple-negative invasive breast cancer, ovarian cancer, or mesothelioma.

In another embodiment, the recombinant CAR fusion protein may be administered to the subject at a concentration which is efficient to modify the immune cells into CAR immune cells in view of the uptake efficiency of the immune cells. For instance, the lower limit of such a concentration may be a concentration which is sufficient for the modified CAR immune cells to show a therapeutic effect for cancer. In addition, the upper limit of such a concentration may be a concentration where the uptake of the recombinant CAR fusion protein by immune cells are saturated. For instance, the recombinant Car fusion protein may be in a concentration of 1,000 nM to 2,000 nM. In another embodiment, the recombinant Car fusion protein may be in a concentration of about 1,000 nM to about 2,000 nM. In another embodiment, the lower limit may be about 1,100 nM, about 1,200 nM, about 1,300 nM, about 1,400 nM, or about 1,500 nM. In another embodiment, the upper limit may be about 1,900 nM, about 1,800 nM, about 1,700 nM, or about 1,600 nM. In another embodiment, the recombinant Car fusion protein may be in a concentration of about 1,000 nM.

The recombinant CAR fusion protein can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a cancer, such as a blood cancer or a solid tumor.

The effective amount can be administered in one or more administrations, applications or dosages and is not intended to be limited to a particular formulation or administration route. In an embodiment, administering is via a course of treatment comprising a plurality of treatment cycles and a plurality of rest periods.

5. The Method of Treating Cancer by Administering the Recombinant CAR Fusion Protein and CAR Immune Cell to a Subject in Need Thereof The present disclosure also provides a method of treating cancer by administering both of the recombinant CAR fusion protein and CAR immune cell discussed above. In particular, in one embodiment, the present disclosure provides a method of treating cancer comprising administering to a subject in need thereof: (i) a recombinant chimeric antigen receptor (CAR) fusion protein comprising, in order, an immune cell targeting domain, a cleavable peptide, a membrane targeting domain, an extracellular cancer targeting domain, a transmembrane domain, and an intracellular signaling domain; and (ii) a CAR immune cell.

In one embodiment, the CAR immune cell is prepared by treating an immune cell with the recombinant CAR fusion protein. In another embodiment, the CAR immune cell may be CAR immune cells prepared by any other methods.

EXAMPLES

Example 1

(A) Preparation of the Recombinant CAR Fusion Protein Against Anti-PD-L1

Figures 1, 8A:
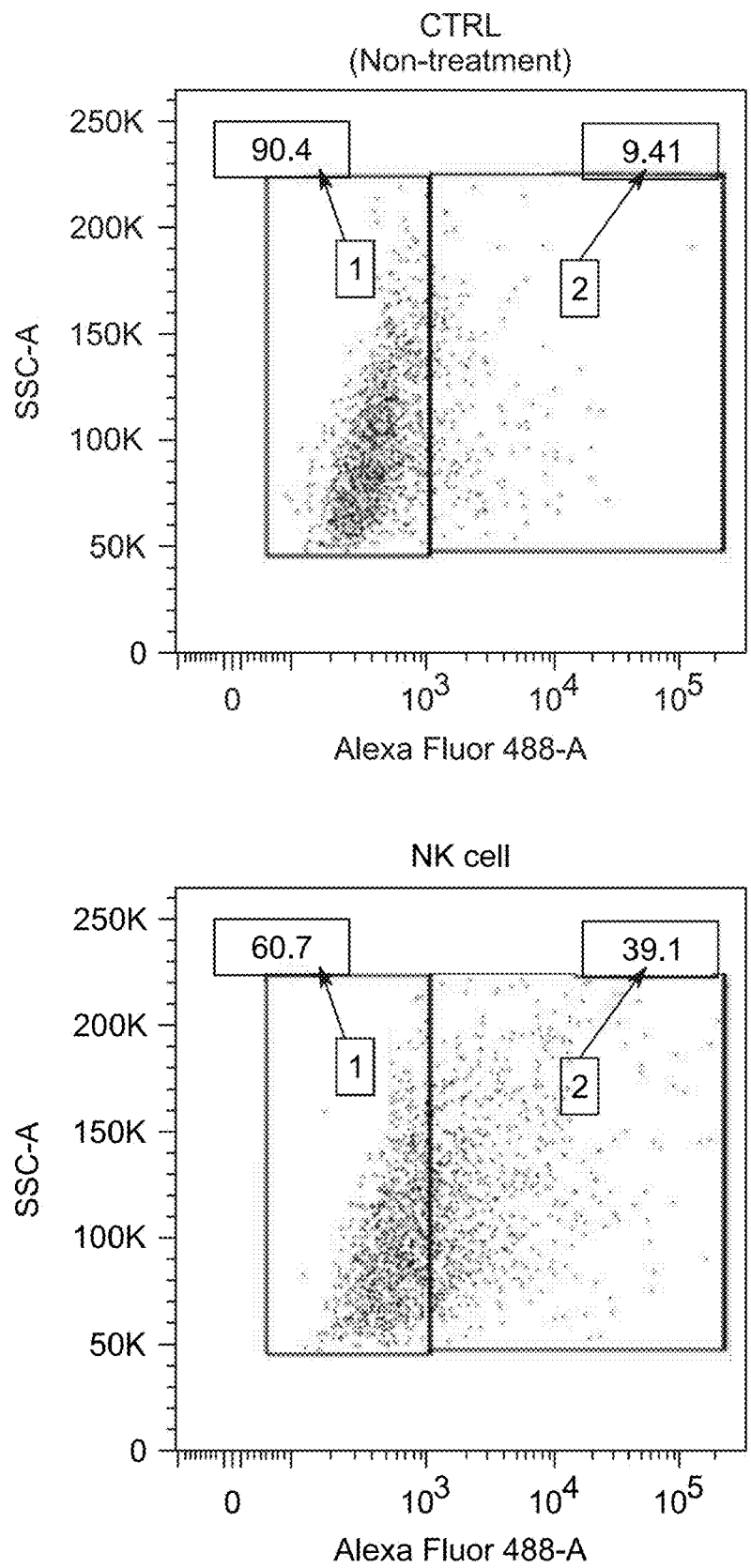
Figures 2, 8A:
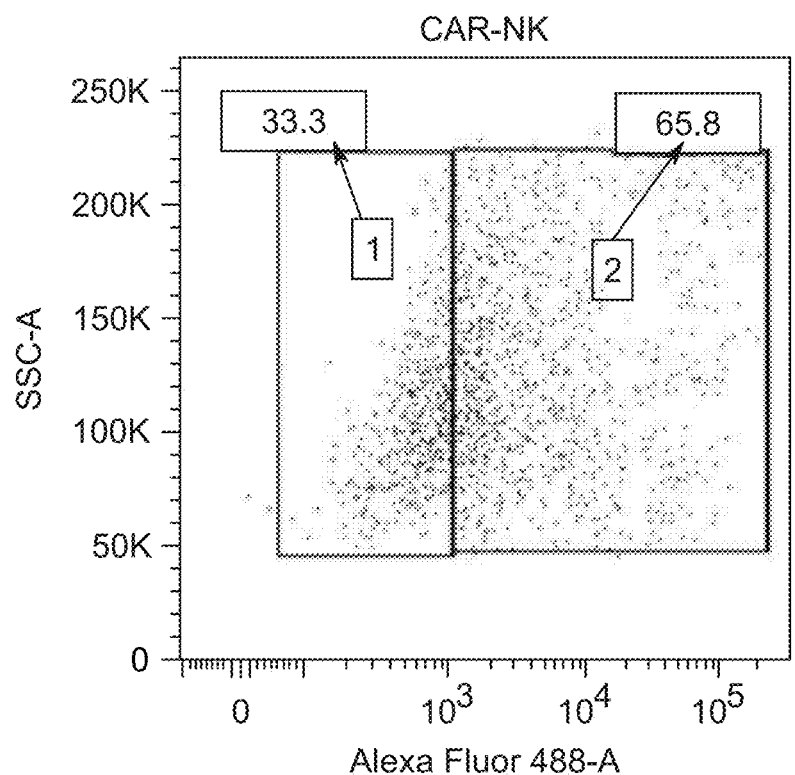

A recombinant CAR fusion protein against anti-PD-L1 was prepared in the following structure.

anti-NKp46 Vh-IgG Hinge-IgG CH2-IgG CH3-linker-Furin-membrane targeting-anti-PD-L1 Vh-CD8 Hinge-NKG2D TM-2B4-CD3 zeta-His tag In particular, the amino acid sequence of the recombinant CAR fusion protein against anti-PD-L1 was as shown in FIG. 1 (SEQ ID NO: 1). The bold letters next to M represent anti-NKp46 Vh-IgG Hinge-IgG CH2-IgG CH3 (i.e., the immune cell targeting domain). The italicized letters represent a GGGGSGGGGSGGGGS (SEQ ID NO: 79) linker and a GGGGS (SEQ ID NO: 69) linker. The bold underlined letters represent a Furin cleavage site (RRAR (SEQ ID NO: 34); i.e., the cleavable peptide). The italicized underlined letters represent a membrane targeting domain. The regular capitalized letters represent anti-PD-L1 Vh (i.e., the extracellular cancer targeting domain). The bold italicized letters represent CD8 hinge (i.e., the hinge region). The underlined letters represent NKG2D (i.e., the transmembrane domain). The smaller letters represent 2B4-CD3 zeta (i.e., the intracellular signaling domain). HHHHHH (SEQ ID NO: 73) at the C-terminal end is the histidine tag (i.e., the tag sequence).

(B) SDS-PAGE and Western Blot Analysis

Figure 3:
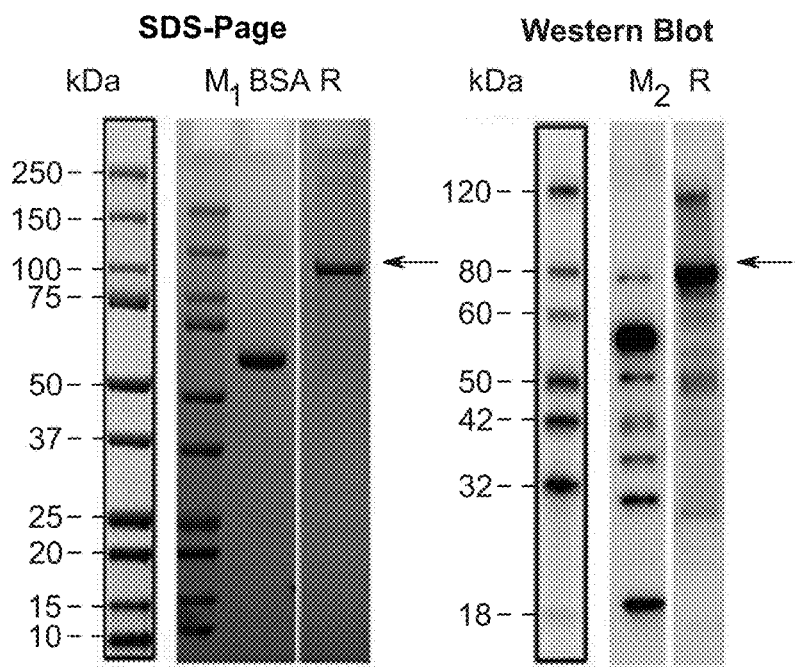
FIG. 3 shows SDS-PAGE and Western blot results.

The in vivo CAR protein was run on SDS-PAGE and western blot to visualize its molecular weight. The molecular weight of the in vivo CAR is 127 kDa, and SDS-PAGE and western blot data show that the band of in vivo CAR protein is around 120 kDa molecular weight marker, indicating well-production of the in vivo CAR protein. See FIG. 3.

Figure 4:
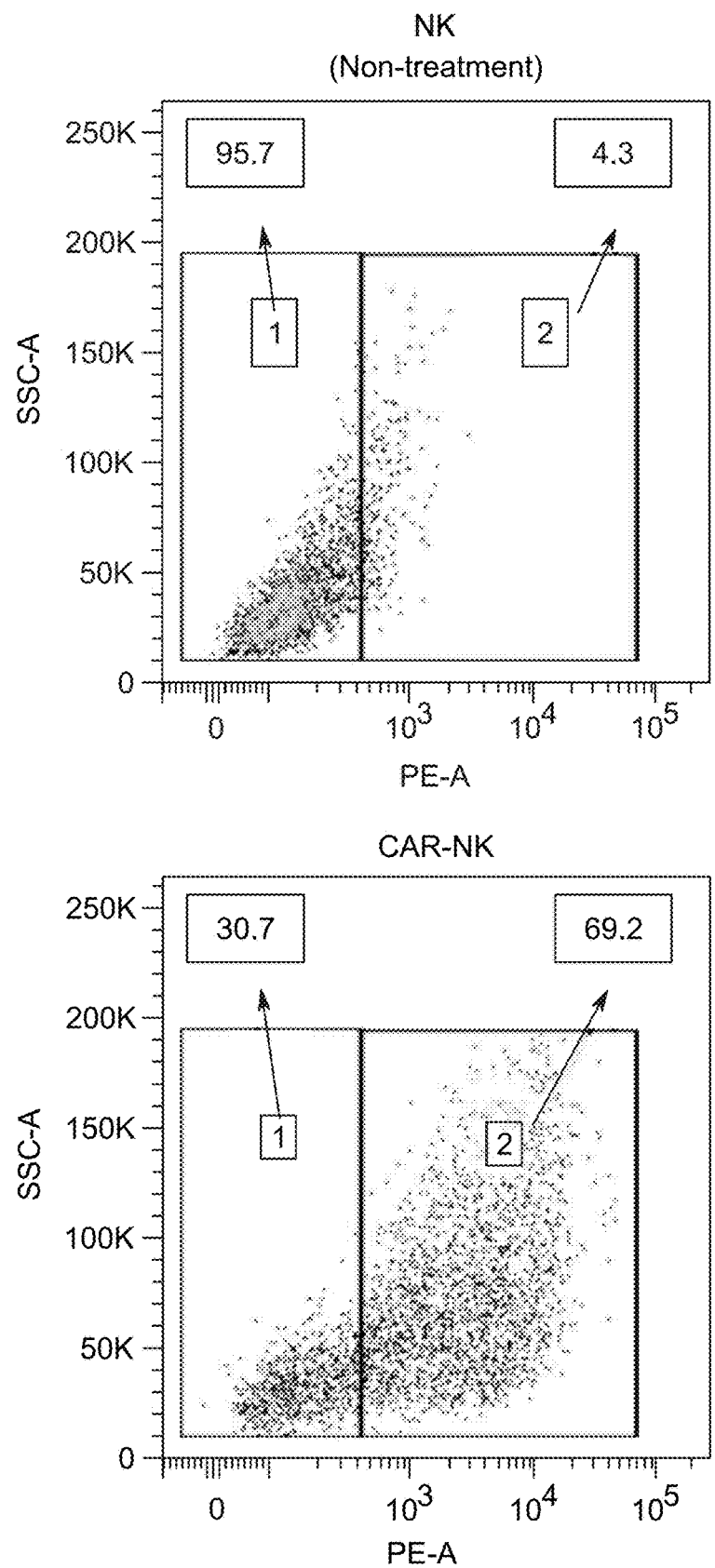
FIG. 4 shows FACS data confirming the uptake of the recombinant CAR fusion protein against anti-PD-L1 by NK cells.

(C) Confirmation of the Uptake of the Recombinant CAR Fusion Protein Against Anti-PD-L1 by NK Cells The prepared recombinant CAR fusion protein against anti-PD-L1 was incubated with NK-92 cells (1 μM of the CAR fusion protein against anti-PD-L1, $1 \times 10^6$ cells/0.5 mL) for 24-hour. The cells were collected and fixed to be permeabilized. Then, PE-conjugated anti-his tag antibody was treated to label his-tag on the recombinant CAR fusion protein against anti-PD-L1. As shown in FIG. 4, it showed that the NK cells treated with the recombinant CAR fusion protein against anti-PD-L1 showed higher PE intensity. The PE-labeled histidine was from with the recombinant CAR fusion protein against anti-PD-L1 since 6× histidine is not naturally presented in cells.

(D) The Recombinant CAR Fusion Protein Transduction Optimization

Figure 5A:
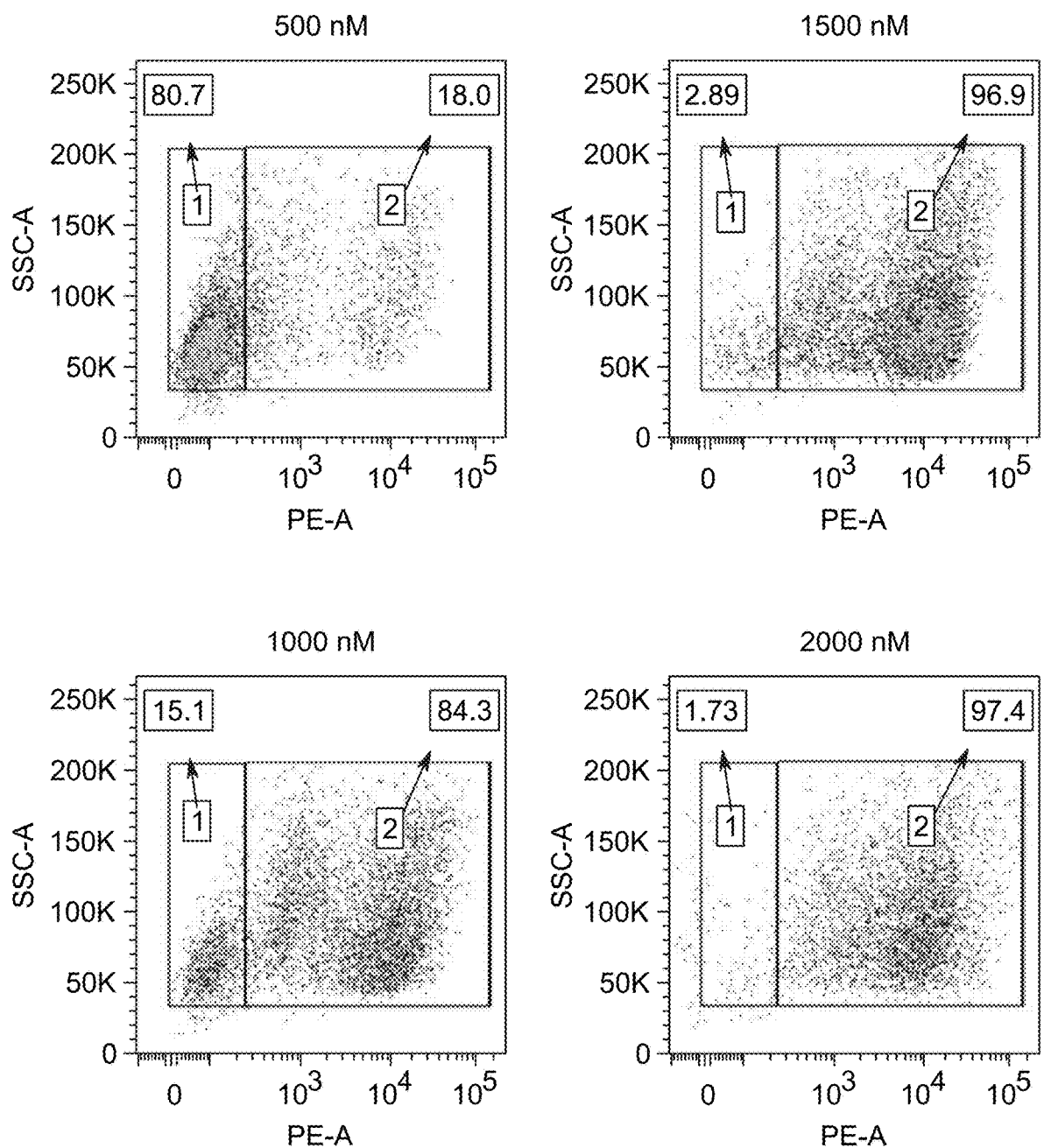
FIGS. 5A and 5B show FACS data comparing the uptake efficiency of the recombinant CAR fusion protein against anti-PD-L1 by NK cells at various concentrations.
Figure 5B:
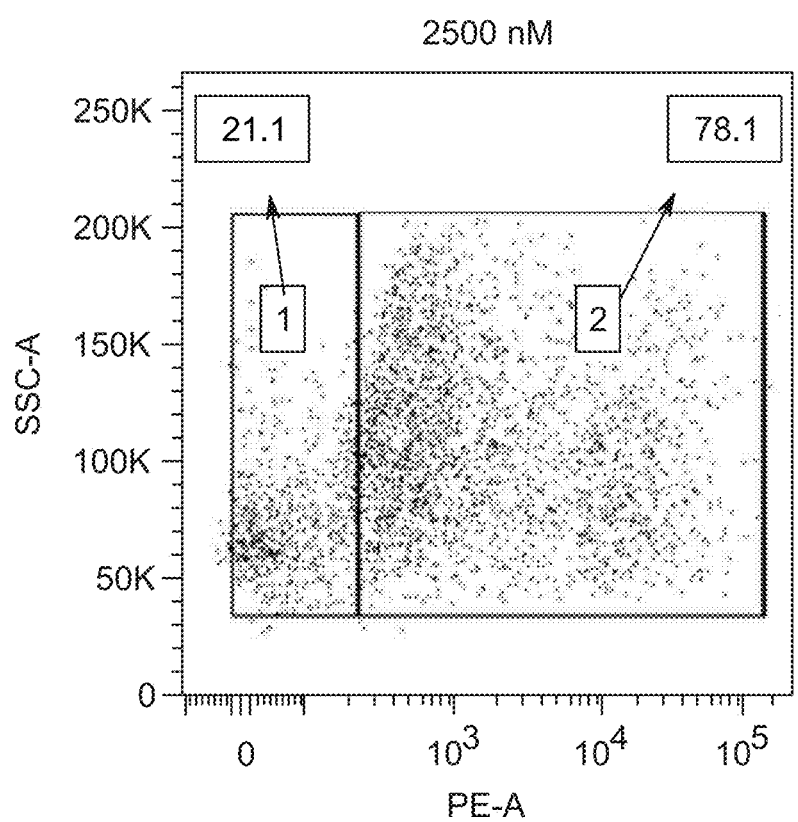

To optimize concentration for the recombinant CAR fusion protein transduction, the recombinant CAR fusion protein with various concentration was treated to NK-92 cells ($1 \times 10^6$ cells/0.5 mL) for 24-hour. Protein transduction was confirmed with same method as discussed under Example 1 (B) above. As shown in FIGS. 5A and 5B, it was confirmed that protein uptake was saturated over 1500 nM. It was speculated that the difference of uptake efficiency between 1000 nM and 1500 nM was not significant to bring the difference on therapeutic efficacy.

(E) The Recombinant CAR Fusion Protein PD-L1 Binding

Figure 6:
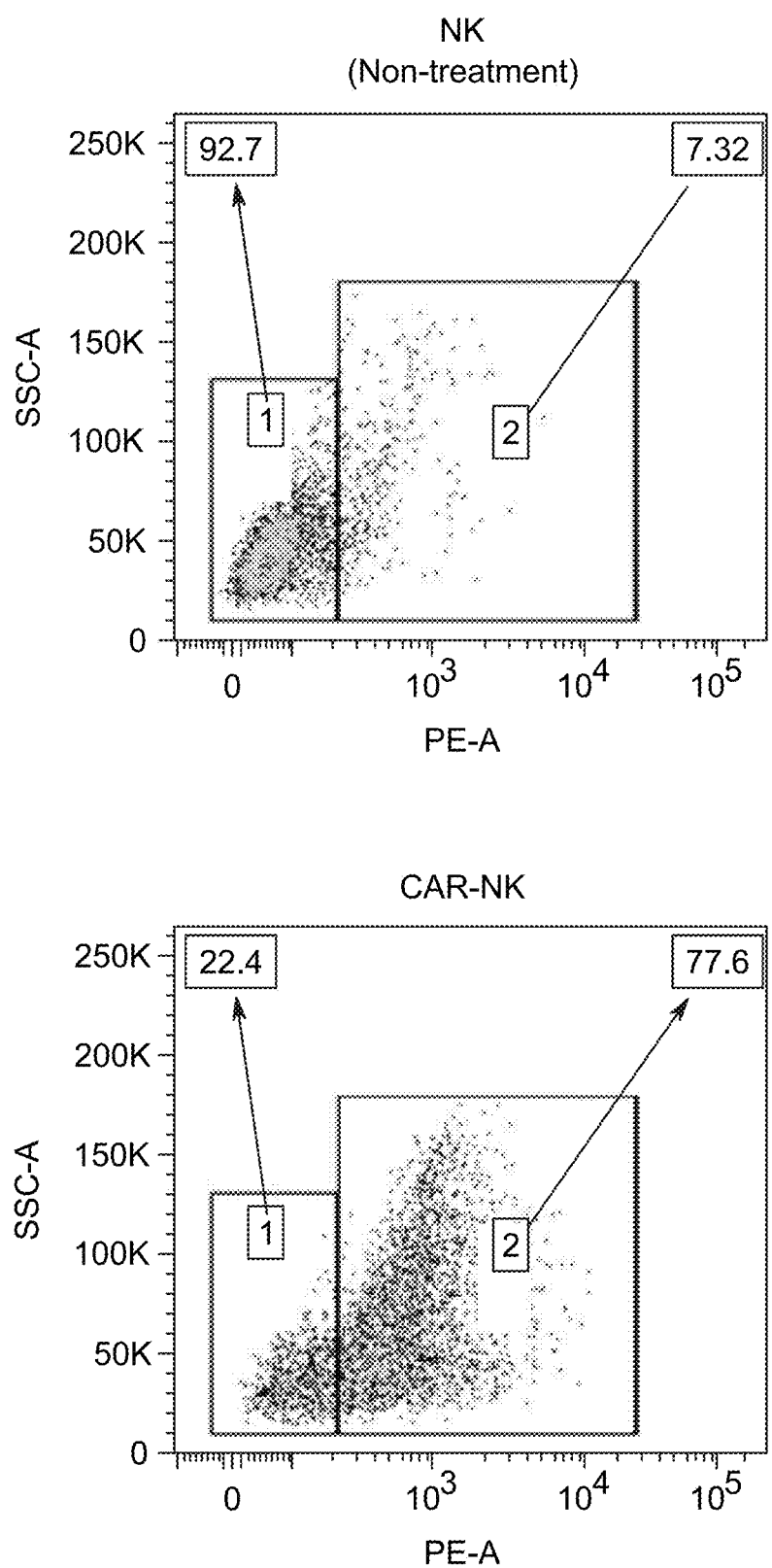
FIG. 6 shows FACS data demonstrating that the CAR-NK cells had higher PE intensity, which indicated that more PD-L1 protein was bound to the CAR-NK cells due to the CAR protein.

After the CAR-NK cells were generated, PD-L1 protein (20 ng/mL) was treated to both of the CAR-NK cells and the NK cells and incubated for 2-hour. Because PD-L1 protein has 6× histidine protein, the PD-L1 protein-bound cells with PE-conjugated anti-his tag antibody were identified. The cells were not permeabilized at this experiment in order to stain exterior his-tag which was conjugated on PD-L1 protein. As shown in FIG. 6, it showed that the CAR-NK cells had higher PE intensity, which indicated that more PD-L1 protein was bound to the CAR-NK cells due to the CAR protein.

(F) Cytokine Release after PD-L1 Binding without Cancer Cell Co-Incubation and Only PD-L1 Treatment.

Figure 7:
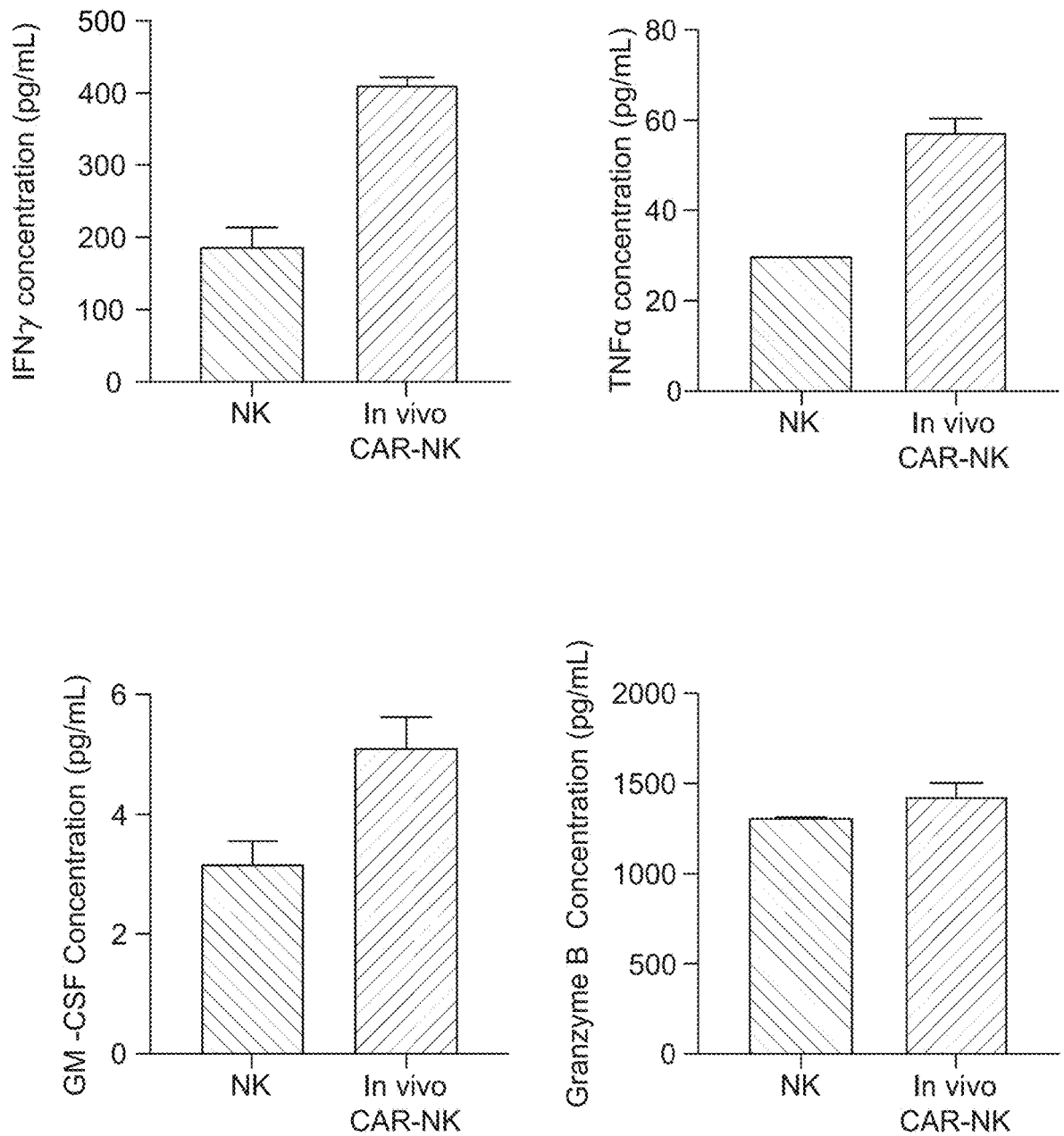
FIG. 7 shows data comparing cytotoxic/cytolytic cytokine secretion upon PD-L1 binding when the CAR-NK cells and the NK cells were treated.

In order to verify the increased anti-cancer activity owing to the CAR fusion protein, cytotoxic/cytolytic cytokine secretion upon PD-L1 binding was analyzed. After PD-L1 binding to the NK cells or CAR-NK cells (2-hour treatment of 20 ng/mL PD-L1 protein), cell supernatant was harvested and ran ELISA. As shown in FIG. 7, it was confirmed that cytokine secretion of the CAR-NK cells were overly increased as compared to that of the NK cells. This result implied that the CAR-NK cells would have stronger anti-cancer activity over the NK cells.

(G) Anti-Cancer Activity of NK Cell: Cancer Cell Death

Anti-cancer activity of the CAR-NK cells and NK cells were compared through induction of cancer cell death. In particular, cancer cells treated with the NK cells, cancer cells treated with the CAR-NK cells, and cancer cells which were not treated with the NK cells or CAR-NK cells were compared. The experiment condition was as follows.

CellTracker Blue™ labelled MDA-MB-231 cancer cells

Effector: Target (E:T)=5:1

Figure 8B:
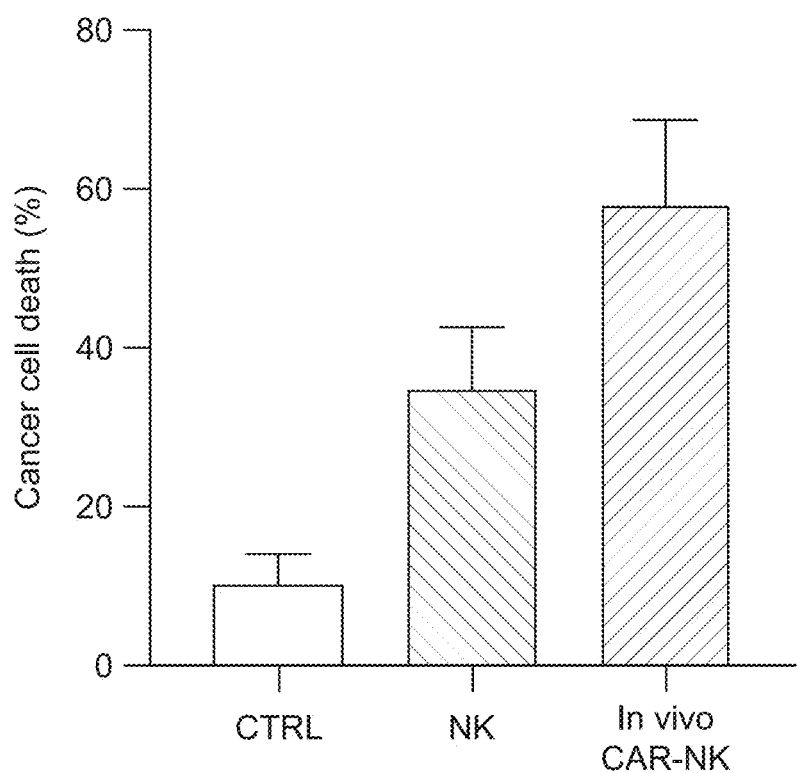

4 hour co-incubation of CellTracker Blue labelled-MDA-MB-231 & NK/In vivo CAR-NK After co-incubation, cells were harvested and stained Alexa Fluor-488 Annexin V to label dead cells. The cells were run through flow cytometry and the population of CellTracker Blue labelled cells (cancer cells) were analyzed intensity of Alexa Fluor 488 (FIGS. 8A-1 and 8A-2). Alexa Fluor 488-Annexin V stained cells indicated dead cancer cells. The more population in number 2 box, the more dead cancer cells. Populations of number 2 box in FIGS. 8A-1 and 8A-2 were summarized in FIG. 8B. These results referred that the CAR-NK cells had stronger anti-cancer activity as compared to the NK cells.

(H) Anti-Cancer Activity of NK Cell: NK Cells' Cytokines

Figure 9:
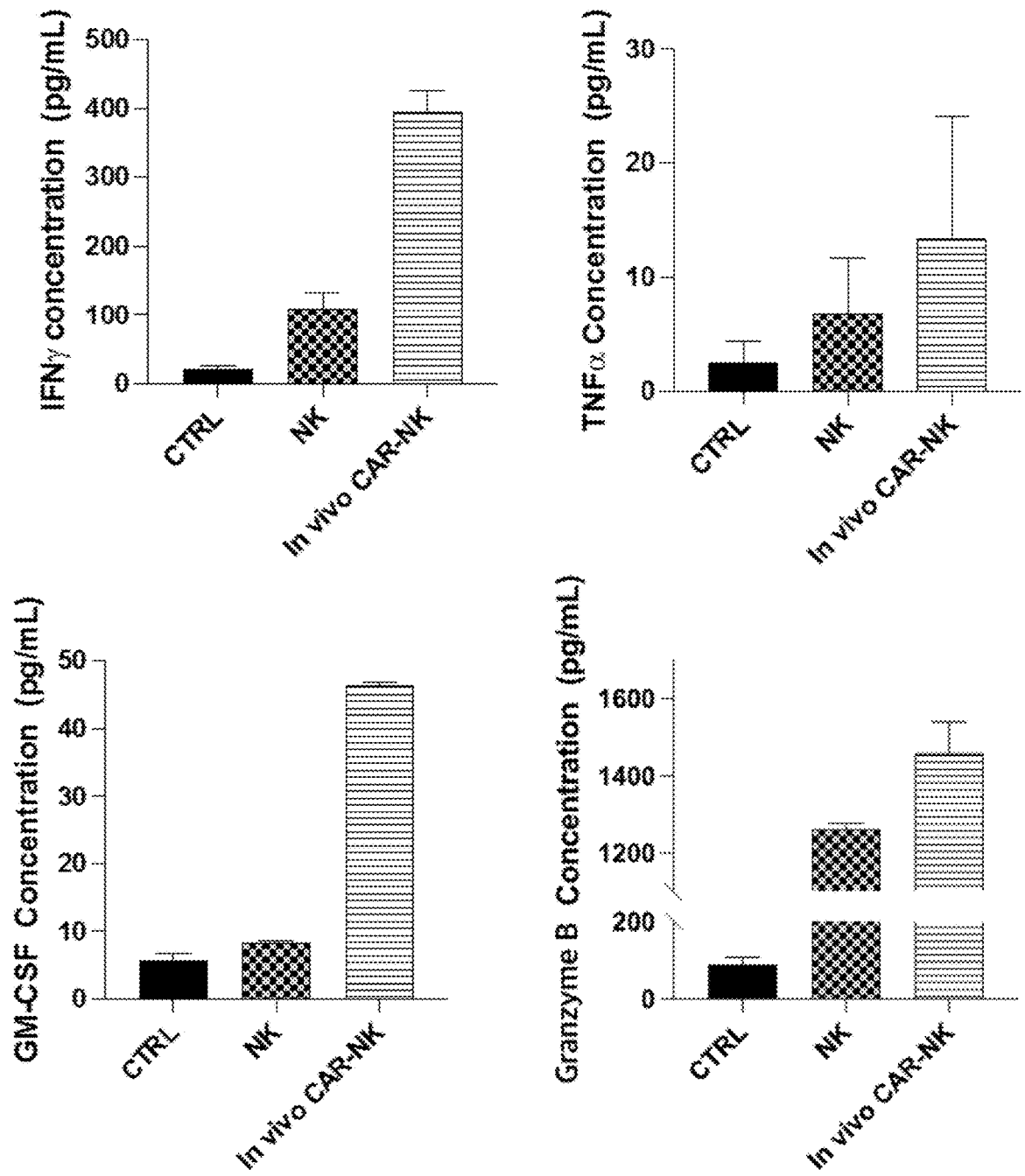
FIG. 9 shows data comparing cytokine secretion when the CAR-NK cells and the NK cells were treated.
Figure 10A:
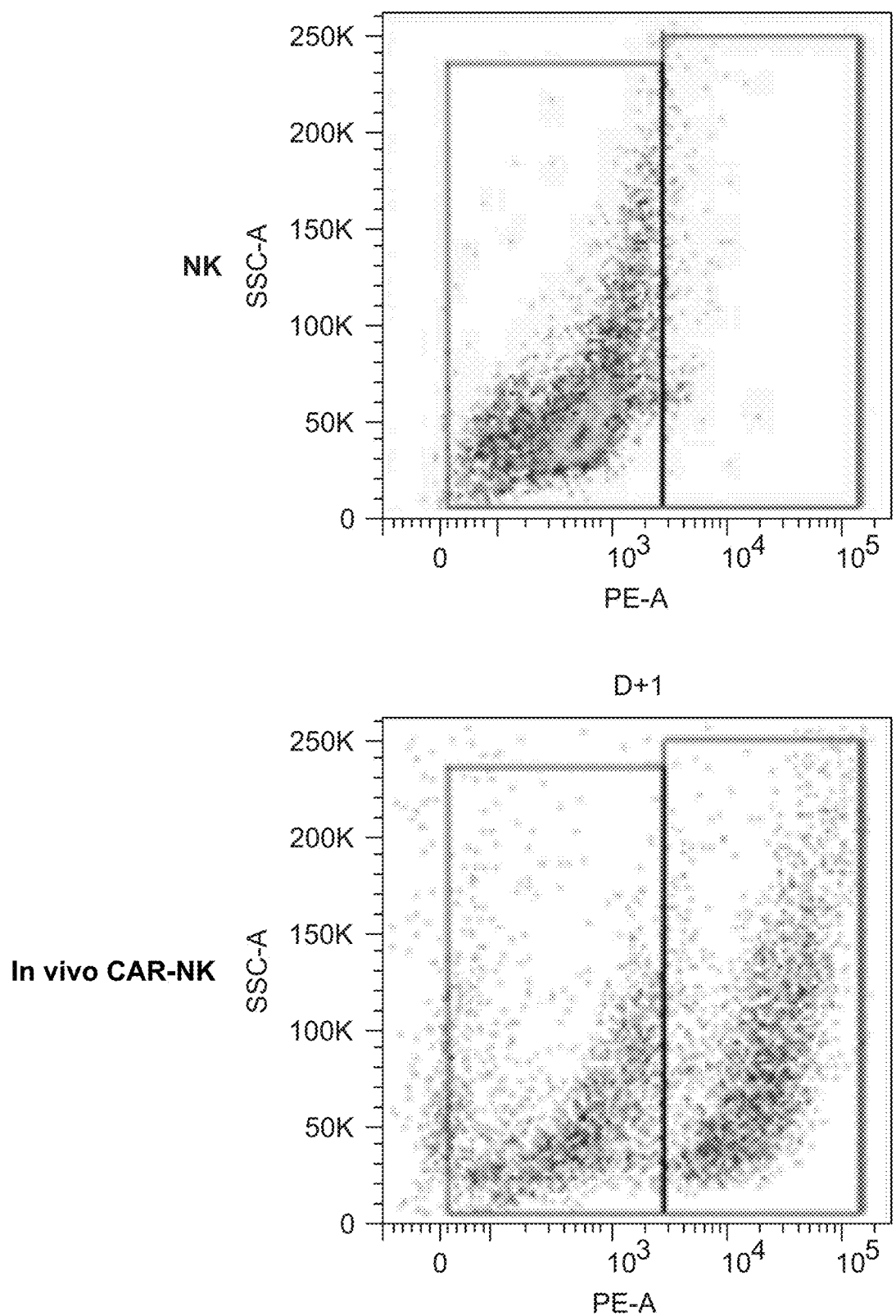
Figures 1, 10B:
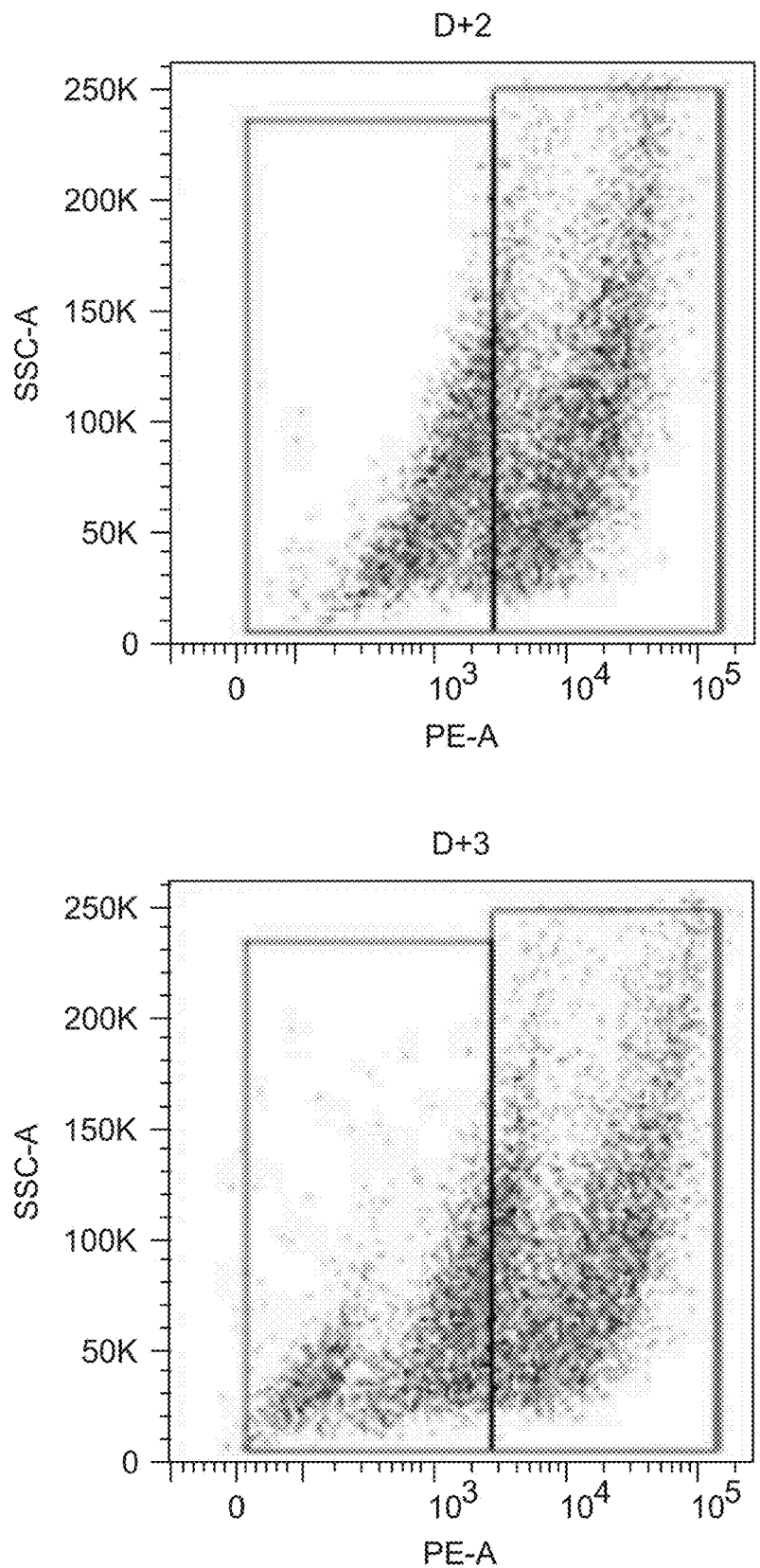
Figure 10B:
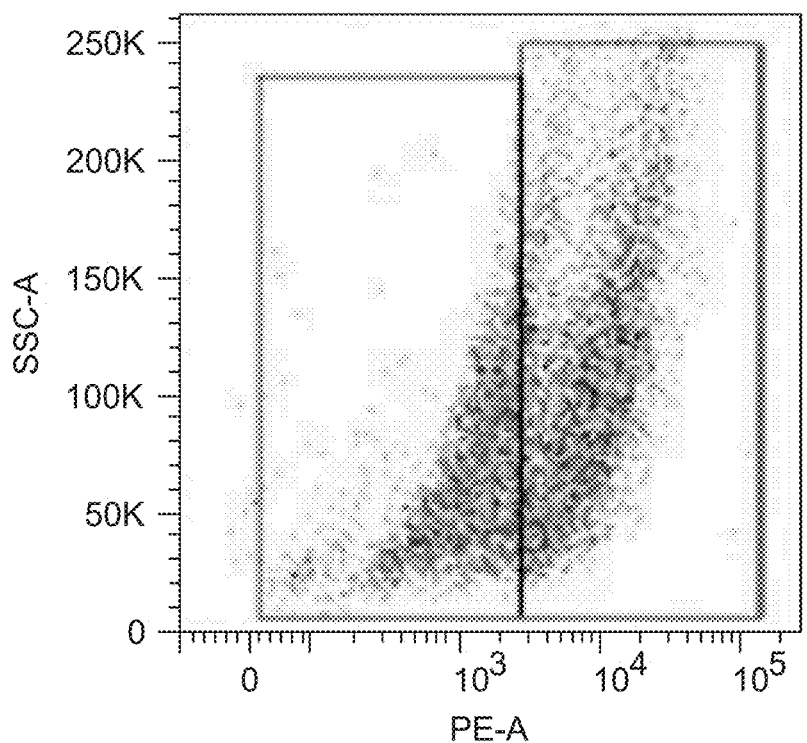
Figure 2:
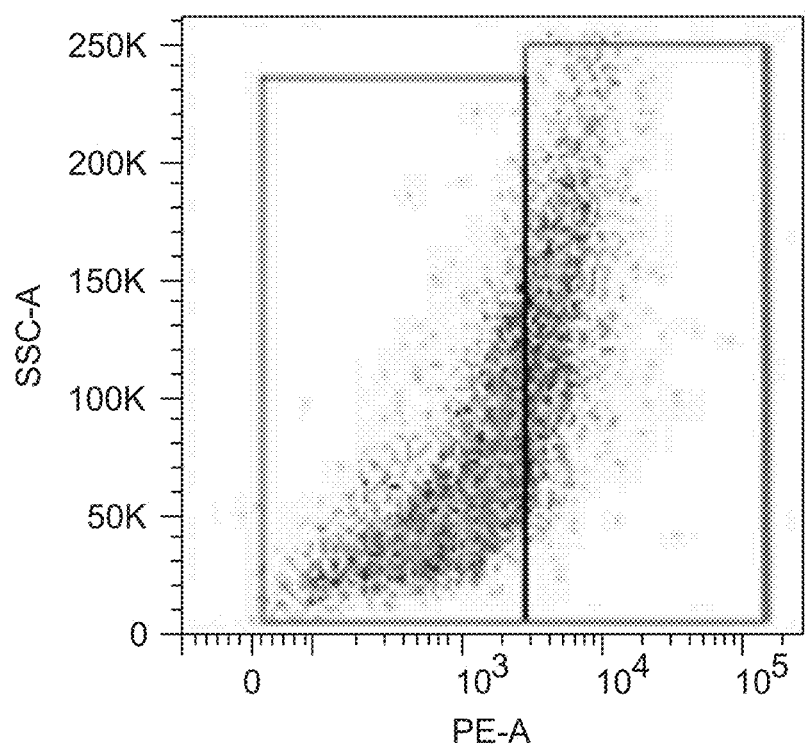
Figure 10C:
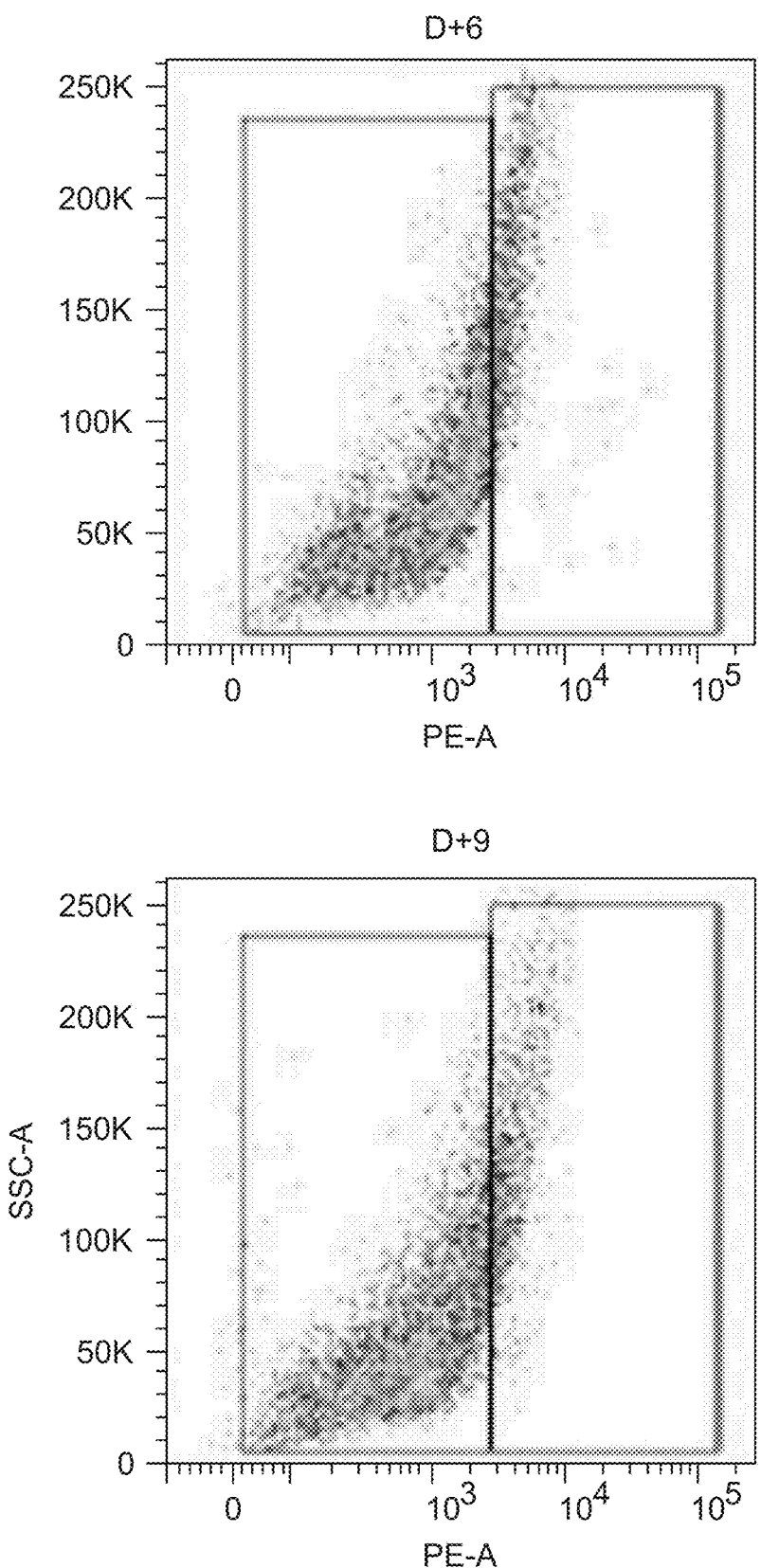

Cytokine secretion from the NK cells and the CAR-NK cells were measured from the cell supernatant after 4 hours co-incubation of cancer cells and the NK cells and the CAR-NK cells. Here, the control group denotes cancer cells which were not treated with the NK cells or CAR-NK cells. The results are shown in FIG. 9. Cytotoxic/cytolytic cytokine were more secreted from and the CAR-NK cells upon cancer cell engraftment than the NK cells. It was confirmed that the increased cancer cell death of the CAR-NK cells were induced by the increased cytokine secretion. Consequently, it was confirmed that the recombinant CAR fusion protein of the present disclosure can modify NK cells to have a CAR system without viral vector-mediated gene transfection and genetic expression time, and consequently, bring the stronger anti-cancer activity.

(I) In Vivo CAR-NK Retention In Vitro

The retention of CAR-NK was confirmed by the intracellular presence of his-tag at the various time points. In vivo CAR-NK cells were generated under the same conditions as other in vitro experiments. The unbound in vivo CAR protein was removed on D+1 using centrifuge process. After the removal of in vivo CAR protein, in vivo CAR-NK cells were incubated in the basic culture condition for NK cells. In vivo CAR-NK cells were collected at the various time points after the treatment of in vivo CAR protein. The collected cells were fixed and permeabilized to label his-tag with PE-conjugated anti-his tag antibody. In vivo CAR-NK cells were detected until D+9. See FIGS. 10A, 10B-1, 10B-2 and 10C.

In vivo CAR Transduction conditions were 1 μM in vivo CAR protein, $1 \times 10^6$ cells/0.5 mL, NK-92 culture medium.

(J) In Vivo Tumor Inhibition by the In Vivo CAR Protein 5 million MDA-MB-231 cells were subcutaneously inoculated in humanized NSG mice. Control group received DPBS, and test groups received 1.7 mg/Kg or 11 mg/Kg in vivo CAR protein intravenously injected once a week for 4 weeks. Tumor volume and body weight was measured twice a week. Tumor volume was measured by caliper measurements (v=0.5ab2; a=long length, b=short length). (A) Relative tumor volume, (B) Relative body weight, and (C) Survival rate. Circle: control group, Square: 1.7 mg/Kg in vivo CAR protein, and Triangle: 11 mg/Kg in vivo CAR protein. (D) Individual relative tumor volume for each group.

Figure 11A:
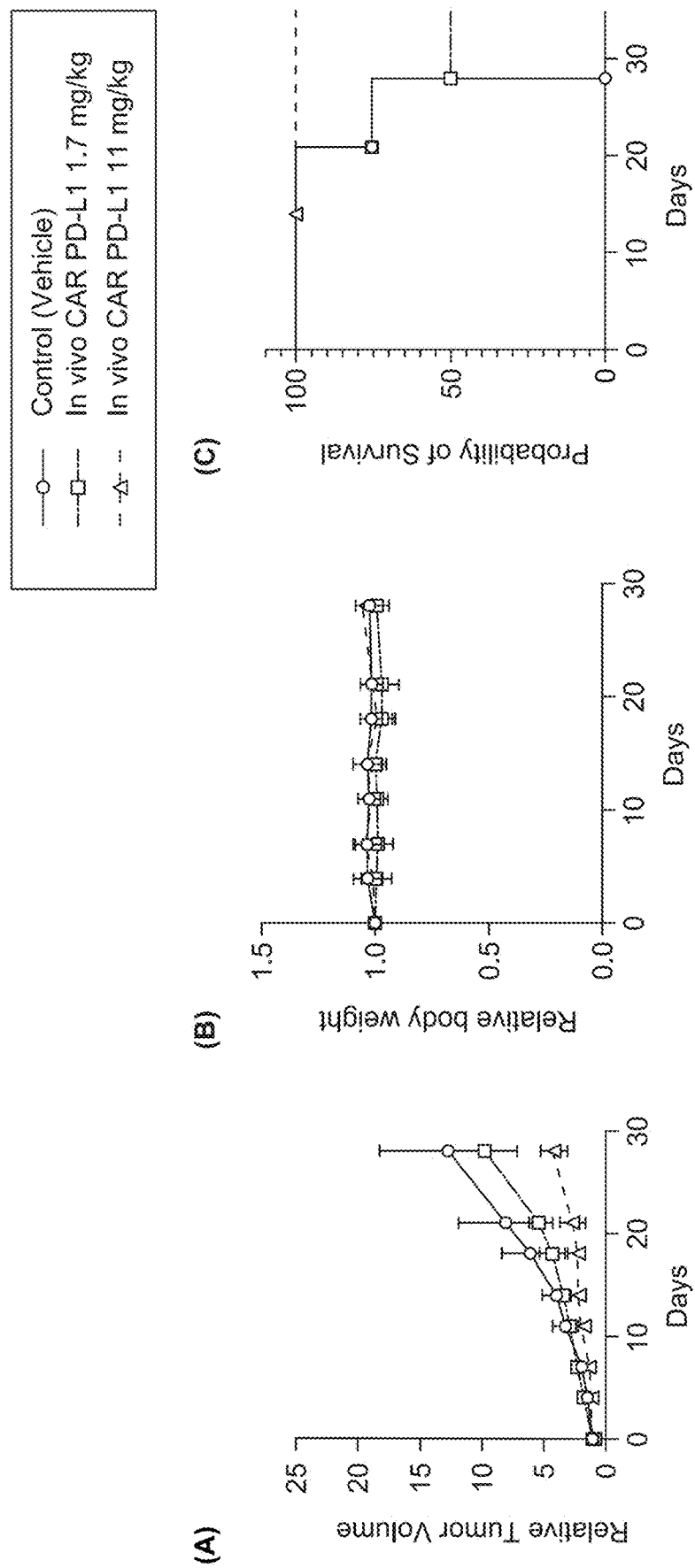
FIGS. 11A and 11B show in vivo tumor inhibition by the in vivo CAR protein.
Figure 11B:
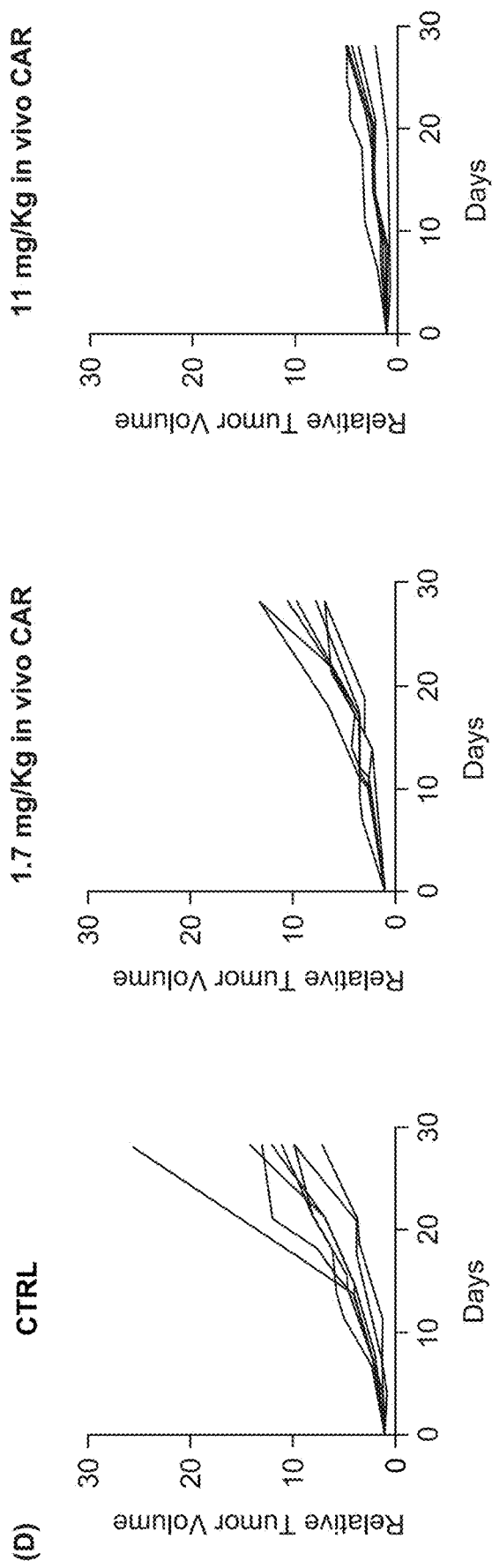

The group of 11 mg/Kg in vivo CAR showed significant tumor inhibition and improved survival rate. The in vivo CAR protein did not affect body weight, indicating safety and non-toxicity. These in vivo experiments demonstrate the therapeutic efficacy and dose-dependency of the in vivo CAR protein. See FIGS. 11A and 11B.

(K) Human Cytokine in Tumor Tissues and Plasma

Figure 12:
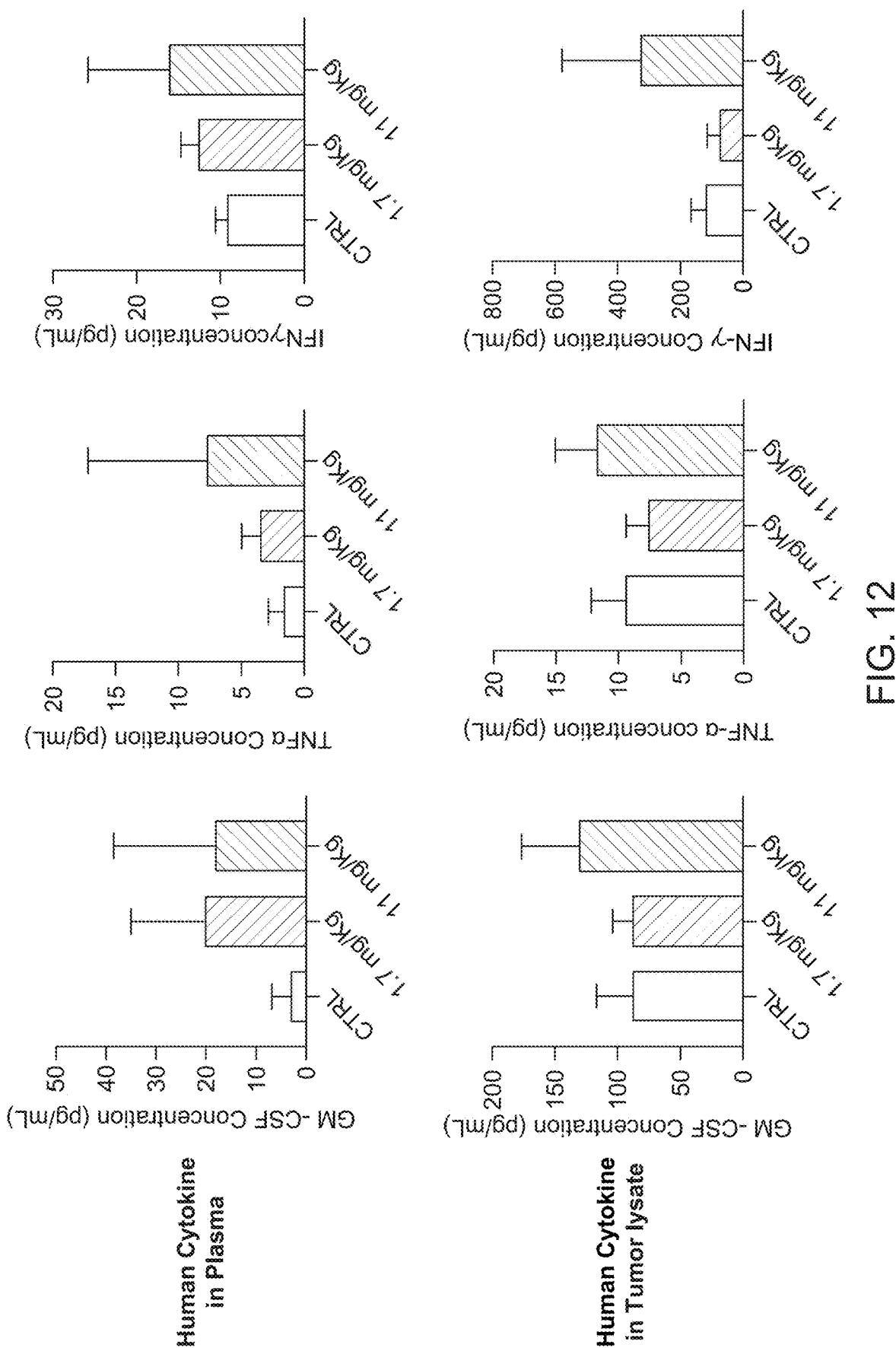
FIG. 12 shows data relating to human cytokine in tumor tissues and plasma.

After the measurement of tumor volume and body weight on D+28, animals were sacrificed to collect blood and organs (tumor, liver, kidney, spleen, and lung). Plasma was subsequently harvested by centrifuge with a gradient medium. To obtain tumor lysate, tumor tissues were homogenized and lysed in RIPA buffer. The supernatant was collected by centrifugation to remove cell debris. Tumor lysate and plasma were run on ELISA kits for human cytokines. In vivo CAR-treated groups demonstrated increasing cytokine secretion. It was hypothesized that the increased concentration of cytokines inhibits tumor progression. This result implies that the in vivo CAR protein induces the activation of the immune system and accounts for its therapeutic efficacy. See FIG. 12.

(L) In Vivo CAR-Modification on Blood Human NK and Human T Cells

Figure 13:
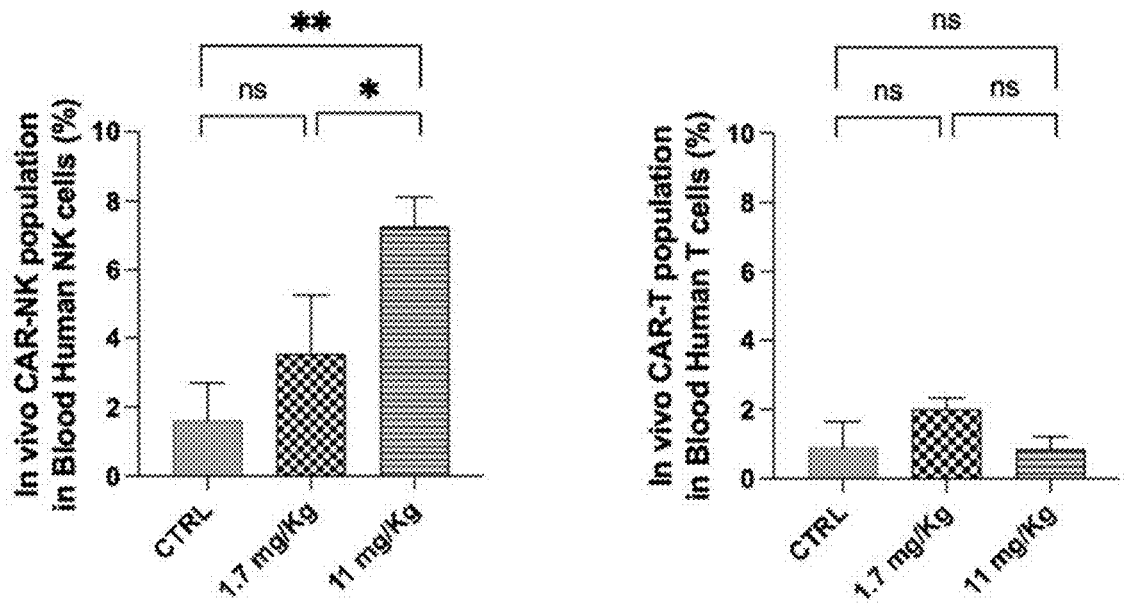
FIG. 13 shows data relating to in vivo CAR-Modification on blood human NK and human T cells.

Blood was collected on D+28 which was 7 days after the last injection of the in vivo CAR protein Immune cells in the blood were harvested through centrifugation with gradient medium and the isolation of human NK cell or human T cells. The isolated human NK and human T cells were fixed and permeabilized to detect in vivo CAR-NK cells or in vivo CAR-T cells by labeling his-tag with PE anti-his tag antibody. The in vivo CAR-NK cells were significantly detected in the in vivo CAR-injected groups, and there was dose-dependency. However, the difference in the in vivo CAR-T population was negligible between the groups. This result indicates that the current in vivo CAR protein specifically modifies NK cells because of its NK cell-targeting domain. Since the in vivo CAR protein has a modular design, the NK cell-targeting domain can be replaced with a T cell-targeting domain for in vivo CAR-T application. See FIG. 13.

(M) NK Cells Become More Cytolytic Upon In Vivo CAR Injection

Figure 14:
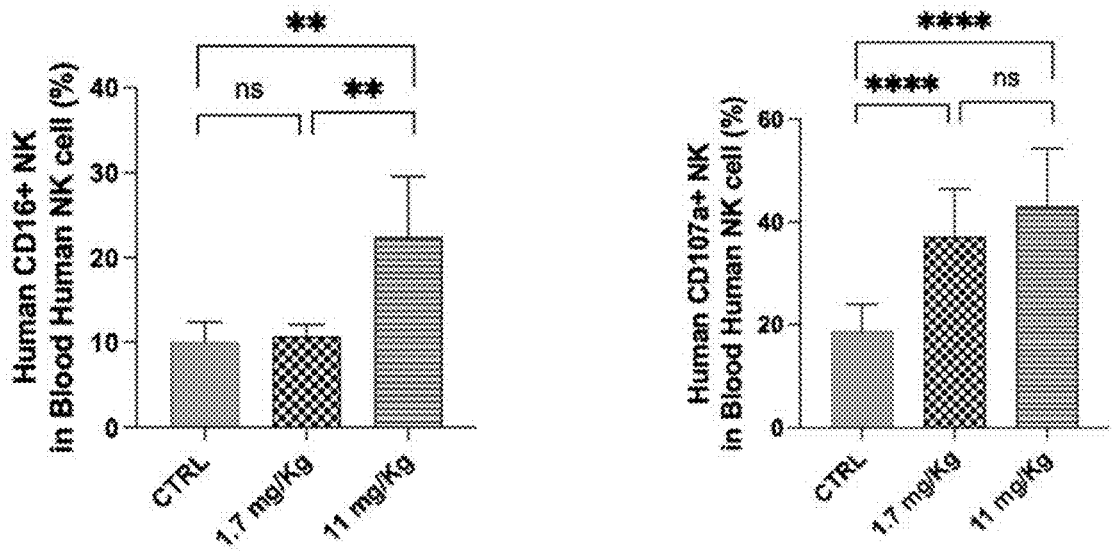
FIG. 14 shows data confirming that NK cells become more cytolytic upon in vivo CAR injection.

Human NK cells isolated from blood were analyzed for their cytolytic characteristics. CD16+NK cells and CD107a+NK cells have cytotoxic features, which are antibody-dependent cellular cytotoxicity (ADCC) and degranulation, respectively. The isolated human NK cells were treated with anti-human CD16 antibody or anti-human CD107a antibody. The population of human CD16+NK cells was increased in the 11 mg/Kg in vivo CAR protein-injected group. The population of human CD107a+NK cells was increased in both of the in vivo CAR protein-injected groups. The results suggest that the in vivo CAR protein stimulates NK cells to have cytolytic characteristics. See FIG. 14.

(N) Initial Liver Toxicity Test

Figure 15:
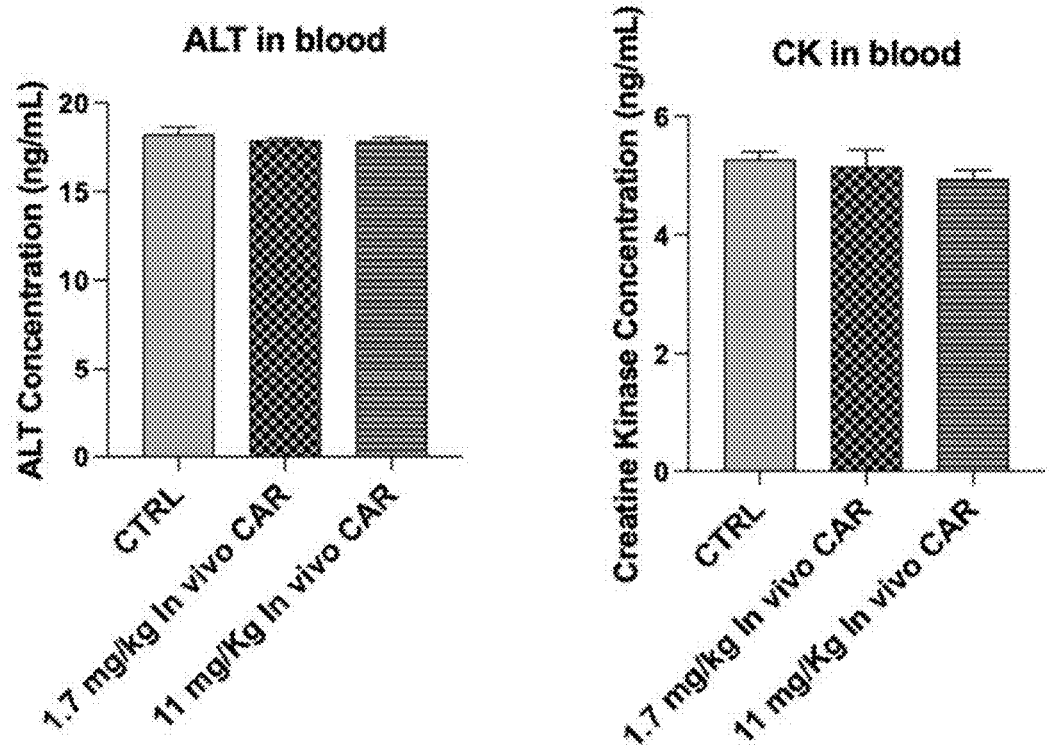
FIG. 15 shows data relating to initial Liver toxicity test.

The levels of alanine transaminase (ALT) and creatine kinase (CK) in blood were analyzed to determine whether the in vivo CAR protein causes liver toxicity. Plasma was run on ELISAs to measure the concentrations of ALK and CK. The injection of the in vivo CAR protein did not result in the elevation of the level of ALT or CK. This result indicates that the injection of the in vivo CAR protein does not cause the liver toxicity. See FIG. 15.

(O) In Vivo CAR Protein Generates a Comprehensive Immune Response in the TME

Figure 16A:
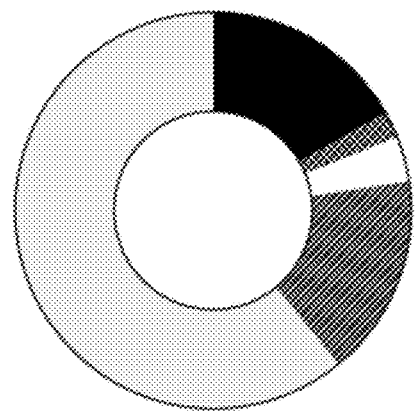
FIGS. 16A, 16B and 16C show data confirming that in vivo CAR protein generates a comprehensive Immune response in the TME.
Figure 16A:
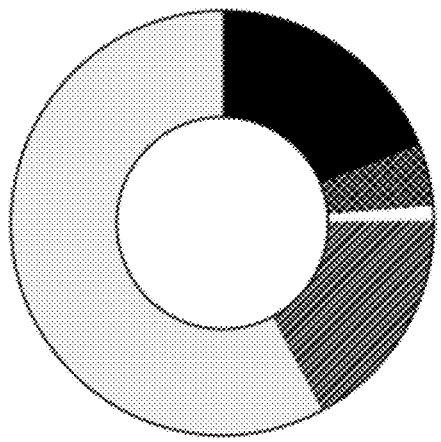
Figure 16A:
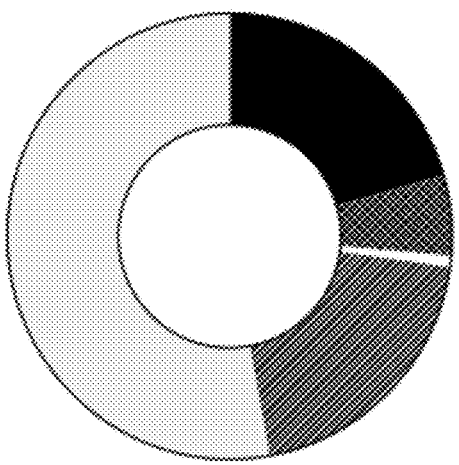
Figure 16B:
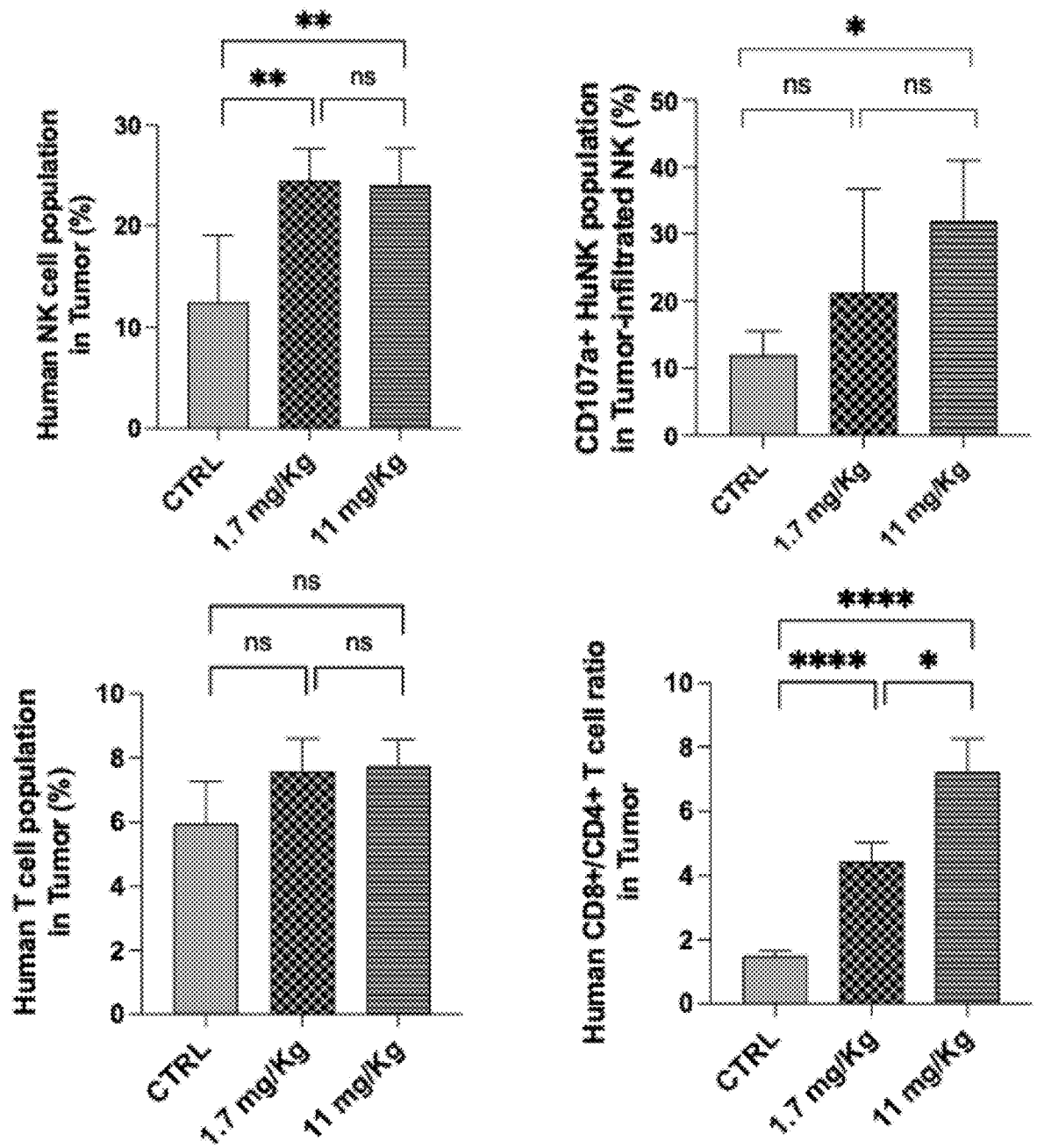
Figure 16C:
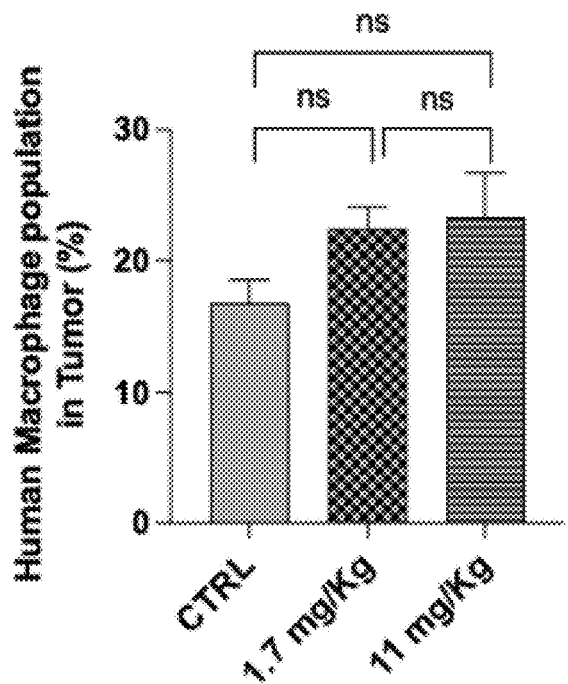
Figure 16C:
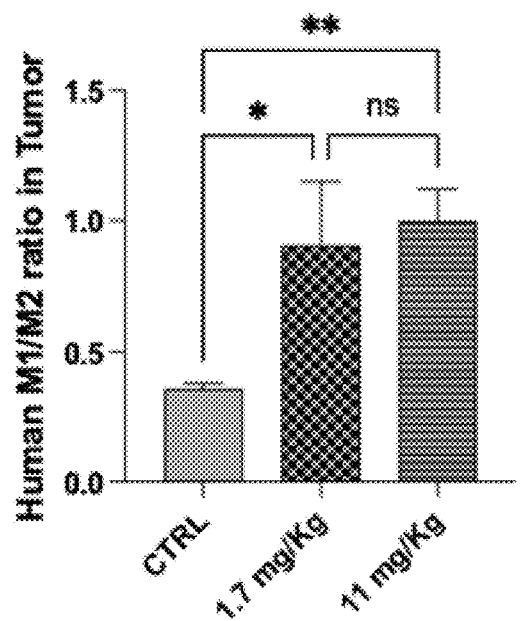

Comprehensive profiling of immune cells in tumor tissue was conducted to characterize the immune response following the administration of the in vivo CAR protein. Tumor tissue was homogenized and dissociated by collagenase to obtain single cells. The single cells were labeled with various antibodies: anti-human CD45 (human hematopoietic marker), anti-human CD56 (human NK cell marker), anti-human CD3 (human T cell marker), anti-human CD4 (helper/regulatory human T cells marker), anti-human CD8 (cytotoxic human T cell marker), anti-human CD68 (human macrophage marker), anti-CD80 (human M1 macrophage marker), and anti-CD206 (human M2 macrophage marker). Administration of the in vivo CAR protein increased the population of tumor-infiltrating human immune cells in the tumor microenvironment (TME) compared to the control group. The in vivo CAR protein specifically modified human NK cells, and the human CAR-NK cells secreted cytokines that reacted with other human immune cells. In addition, both the in vivo CAR protein-injected groups had significantly increased ratios of human CD8+/CD4+ T cells and human M1/M2 macrophages. Therefore, it was confirmed that the in vivo CAR protein induces a comprehensive immune response in the TME. The population of human CD107a+NK cells in the TME was also increased in both in vivo CAR-injected groups. These results are in line with the data confirming the increased population of human CD107a+NK cells in blood. Taken together, these results indicate that the in vivo CAR protein generates a comprehensive immune response in the TME, accounting for its promising therapeutic efficacy. See FIGS. 16A, 16B and 16C.

(P) Initial Immunogenicity Test

Figure 17:
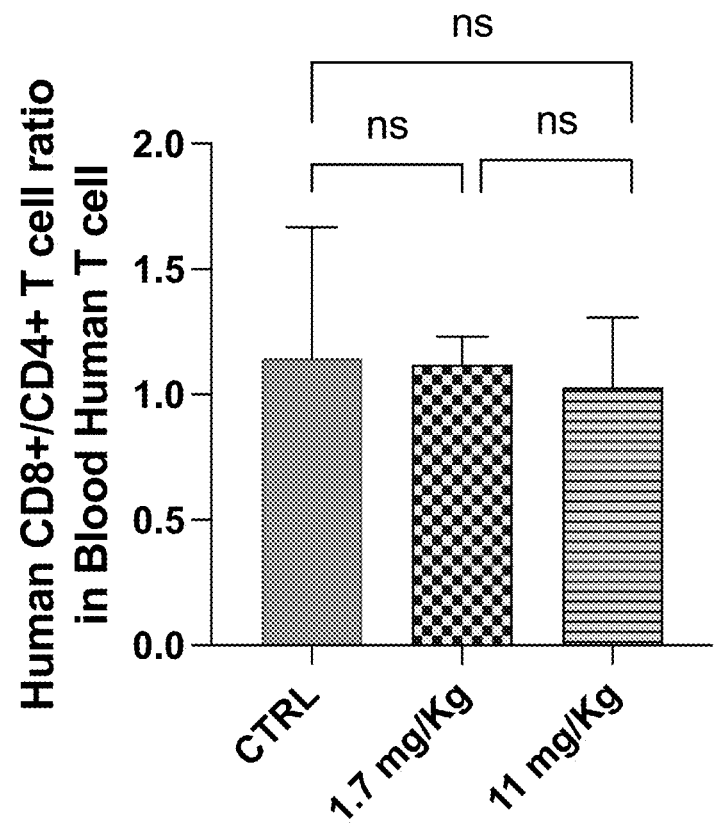
FIG. 17 shows data relating to initial immunogenicity test.

To address the potential immunogenicity of the in vivo CAR protein, the ratio of CD8+/CD4+ human T cells in the blood was analyzed. The induction of immunogenicity would result in the proliferation of CD4+ T cells, thereby changing the ratio of CD8+/CD4+ human T cells. It was found that the in vivo CAR-injected groups had insignificant differences in the ratio of CD8+/CD4+ human T cells compared to the control group, indicating that they did not cause immunogenicity. See FIG. 17.

(Q) In Vivo CAR-NK Biodistribution

Figure 18:
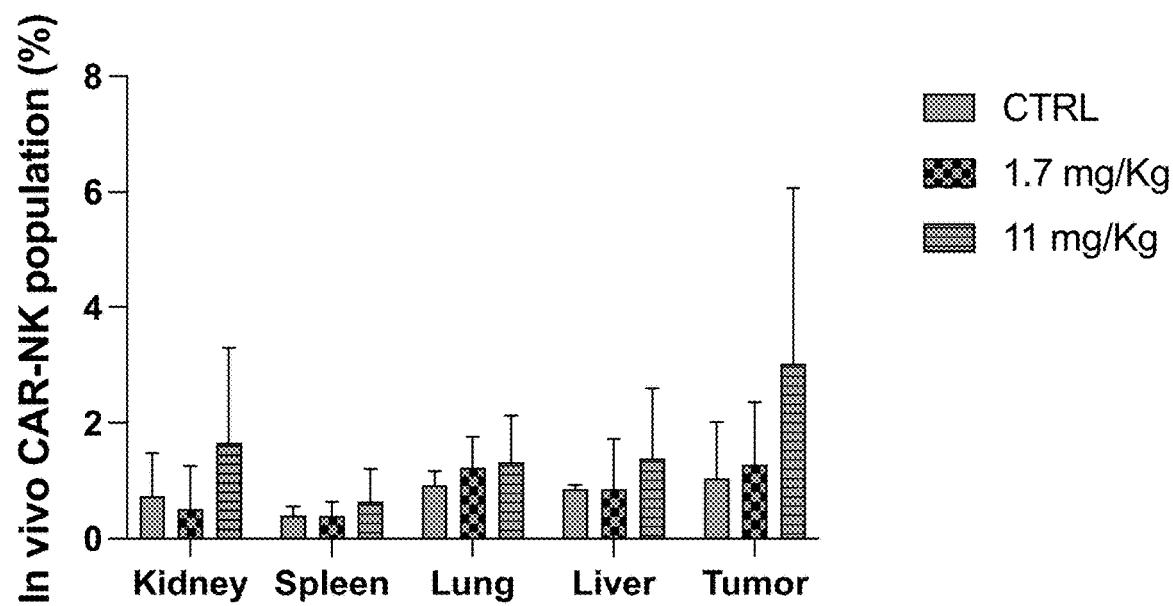
FIG. 18 shows data relating to in vivo CAR-NK biodistribution.

To analyze the biodistribution of the in vivo CAR-NK cells, organs including kidney, spleen, lung, liver and tumor were isolated on D+28, which was 7 days after the final in vivo CAR infusion. Tumor tissues were homogenized and dissociated by collagenase to obtain single cells. The cells were fixed and permeabilized to label intracellular his-tag. PE-conjugated anti-his tag antibody was treated to the cells, and the cells were analyzed by flow cytometry. In the 11 mg/Kg in vivo CAR-injected group, the population of in vivo CAR-NK cells increased in the tumor tissues compared to the other tissues. This data demonstrates that in vivo CAR protein modifies NK cells into CAR-NK cells, and reliably directs those cells to the tumor. See FIG. 18.

As discussed above, the recombinant CAR fusion protein against anti-PD-L1 expressed on various cancer cells was firstly created and presented in the present disclosure. It was verified that this recombinant CAR-PDL1 protein spontaneously modifies NK cells into CAR-NK PDL1. The resulting CAR-NK PDL1 captures PD-L1 protein (antigen) more efficiently than naïve NK cells, resulting in an increase in the secretion of cytotoxic/cytolytic cytokines upon PD-L1 binding. This result indicates that CAR-NK PDL1 is successfully generated and able to recognize its complementary antigen.

It was also verified the more than twice stronger anti-cancer activity and significantly enhanced secretion of cytokines after co-culture of CAR-NK PDL1 with triple-negative breast cancer cells, which express PD-L1. Consequently, it was confirmed that the recombinant CAR fusion protein modifies immune cells into CAR-immune cells and can be developed for both of in vivo and ex vivo applications.

Example 2

(A) Preparation of the Recombinant CAR Fusion Protein Against Anti-PD-L1

A recombinant CAR fusion protein for T cell against anti-PD-L1 is designed with mixing the T cell targeting antibody and intracellular stimulatory region from following table.

TABLE 2

(T cell surface marker for Immune cell-targeting antibody region and intracellular stimulator for intracellular region of In vivo CAR-T)

| T cell targeting domain | T cell transmembrane domain | T cell intracellular simulator domain |
|---|---|---|
| CD3 | CD3 | CD3 ζ |
| CD4 | CD8 | CD28 |
| CD5 | CD28 | 4-1BB |
| CCR7 (CD8+ Cytotoxic T) | | CD40 |
| CD107a (CD8+ Cytotoxic T) | | OX-40 |
| CD28 (CD8+ Cytotoxic T) | | CD27 |
| CD45RA (CD8+ Cytotoxic T) | | ICOS |
| CD8 (CD8+ Cytotoxic T) | | DAP12 |
| CD95 (CD8+ Cytotoxic T) | | FcRγ |
| FasL (CD8+ Cytotoxic T) | | CD8 |
| TRAIL (CD8+ Cytotoxic T) | | CD4 |
| 2B4 (Ex-T) | | ITAM |
| BTLA (Ex-T) | | TLR2 |
| CD160 (Ex-T) | | IL2Rb |
| CD226 (Ex-T) | | STAT3-binding motif |
| CD96 (Ex-T) | | |
| CTLA4 (Ex-T) | | |
| GITR (Ex-T) | | |
| LAG-3 (Ex-T) | | |
| PD-1 (Ex-T) | | |
| TIGIT (Ex-T) | | |
| TIM-3 (Ex-T) | | |
| VISTA (Ex-T) | | |
| TCRγ/δ (γδT) | | |
| IL23 Receptor (γδT) | | |
| TCR Vα24 (NKT) | | |
| TCR Vβ11 (NKT) | | |

The CAR fusion protein for T cells is prepared in the following structure.

Anti-T cell targeting antibody Vh-IgG Hinge-IgG CH2-IgG CH3-linker-Furin-membrane targeting-anti-PD-L1 Vh-CD8 Hinge-Transmembrane region-Intracellular region 1-CD3 zeta-His tag (B) Confirmation of the Uptake of the Recombinant CAR Fusion Protein Against Anti-PD-L1 by T Cells The recombinant CAR fusion protein against anti-PD-L1 is incubated with T cells (1 μM of the CAR fusion protein against anti-PD-L1, $1 \times 10^6$ cells/0.5 mL) for 24-hour. The cells are collected and fixed to be permeabilized. Then, PE-conjugated anti-his tag antibody is treated to label his-tag on the recombinant CAR fusion protein against anti-PD-L1. It is expected that the T cells treated with the recombinant CAR fusion protein against anti-PD-L1 show higher PE intensity. The PE-labeled histidine is from with the recombinant CAR fusion protein against anti-PD-L1 since 6× histidine is not naturally presented in cells.

(C) The Recombinant CAR Fusion Protein Transduction Optimization

To optimize concentration for the recombinant CAR fusion protein transduction, the recombinant CAR fusion protein with various concentration is treated to T cells ($1 \times 10^6$ cells/0.5 mL) for 24-hour. Protein transduction is confirmed with same method as discussed under Example 2 (B) above. The result is anticipated that the protein uptake is saturated over 1500 nM as like CAR fusion protein transduction to NK cells, and 1000 nM is selected as the optimal transduction concentration.

(D) The Recombinant CAR Fusion Protein PD-L1 Binding

After the CAR-T cells are generated, PD-L1 protein is treated to both CAR-T cells and the T cells and incubated for 2-hour. Because PD-L1 protein has 6× histidine protein, the PD-L1 protein-bound cells with PE-conjugated anti-his tag antibody are identified. The cells are not permeabilized at this experiment in order to stain exterior his-tag which is conjugated on PD-L1 protein. It is expected that the CAR-T cells have higher PE intensity, which indicates that more PD-L1 protein is bound to the CAR-T cells than normal T cells due to the CAR protein.

(E) Cytokine Release after PD-L1 Binding Through PD-L1 Protein Treatment without Cancer Cell Co-Incubation.

In order to verify the increased anti-cancer activity owing to the CAR fusion protein, cytotoxic/cytolytic cytokine secretion upon PD-L1 binding to CAR-T and T cells is analyzed. After PD-L1 binding to the T cells or CAR-T cells (2-hour treatment of 20 ng/mL PD-L1 protein), cell supernatant is harvested and ran cytokine ELISA as like CAR-NK cell analysis. It is anticipated that cytokine secretion of the CAR-T cells are overly increased as compared to that of the T cells. This result implies that the CAR-T cells have stronger anti-cancer activity over the T cells.

(F) Anti-Cancer Activity of T Cell: Cancer Cell Death

Anti-cancer activity of the CAR-T cells and T cells are compared through induction of cancer cell death. The experiment condition is as follows.

CellTracker Blue™ labelled MDA-MB-231 cancer cells

Effector: Target (E:T)=5:1

4 hour co-incubation of CellTracker Blue™ labelled-MDA-MB-231 & T cells/30 In vivo CAR-T cells After co-incubation, cells are harvested and stained Alexa Fluor-488 Annexin V to label dead cells. The cells are run through flow cytometry and the population of CellTracker Blue™ labelled cells (cancer cells) are analyzed the intensity of Alexa Fluor 488. Alexa Fluor 488-Annexin V stained cells indicate dead cancer cells. The more population of Alexa Fluor 488-stained cells, the more dead cancer cells. It is predicted that that the CAR-T cells had stronger anti-cancer activity as compared to the T cells.

(G) Anti-Cancer Activity of T Cell: T Cells' Cytokines

Cytokine secretion from the T cells and the CAR-T cells are measured from the cell supernatant after 4 hours co-incubation of cancer cells with the T cells or the CAR-T cells. The result is expected that cytotoxic/cytolytic cytokines are more secreted from and the CAR-T cells upon cancer cell engraftment than the T cells. The cytokine result is anticipated to have correlation with cancer cell death to demonstrate that the increased cancer cell death of the CAR-T cells are induced by the increased cytokine secretion. Consequently, it is anticipated that the recombinant CAR fusion protein can modify T cells to have a CAR system without viral vector-mediated gene transfection and genetic expression time, and consequently, bring the stronger anti-cancer activity.

---

The invention claimed is:

1. A recombinant chimeric antigen receptor (CAR) fusion protein comprising, in order:
- an immune cell targeting domain, the immune cell targeting domain being a NK cell targeting domain, or a T cell targeting domain,
- a cleavable peptide,
- a membrane targeting domain, the membrane targeting domain being a peptide from interleukin-1 receptor type 1, 4F2 cell-surface antigen heavy chain, a linker for activation of T-cells family member 1, junctophilin-1, antilisterial bacteriocin subtilosin biosynthesis protein AlbG, calcitonin receptor, gamma-secretase subunit APH-1A, or adipnectin receptor protein 2,
- an extracellular cancer targeting domain,
- a transmembrane domain, and
- an intracellular signaling domain.

2. The recombinant CAR fusion protein of claim 1, wherein the NK cell targeting domain is a NK cell-targeting-scFv antibody, or a peptide comprising an anti-NKp46 VH, IgG hinge, IgG CH2 and IgG CH3.

3. The recombinant CAR fusion protein of claim 1, wherein the cleavable peptide is a peptide which is configured to be enzymatically cleaved.

4. The recombinant CAR fusion protein of claim 1, wherein the extracellular cancer targeting domain is an anti-PD-L1 Vh.

5. The recombinant CAR fusion protein of claim 1 further comprising a hinge region between the extracellular cancer targeting domain and the transmembrane domain.

6. The recombinant CAR fusion protein of claim 1, wherein the transmembrane domain is NKG2D.

7. The recombinant CAR fusion protein of claim 1, wherein the intracellular signaling domain comprises a CD3 zeta (CD3ξ) signaling domain and a co-stimulatory signaling region selected from the group consisting of 2B4, DAP12, GITR, CD137, OX40.

8. The recombinant CAR fusion protein of claim 1 further comprising a tag sequence.

9. The recombinant CAR fusion protein of claim 8, wherein the tag sequence is selected from the group consisting of a histidine tag, glutathione-S-transferase tag, or hemagglutinin tag.

10. A method of modifying an immune cell into a chimeric antigen receptor (CAR) immune cell, comprising treating the immune cell with the recombinant CAR fusion protein of claim 1.

11. The method of claim 10, wherein the recombinant CAR fusion protein is in a concentration of about 1,000 nM to about 2,000 nM.

12. A method of treating cancer comprising administering the CAR immune cell of claim 10 to a subject in need thereof.

13. A method of treating cancer comprising administering the recombinant CAR fusion protein of claim 1 to a subject in need thereof.

14. The method of claim 13, wherein the recombinant CAR fusion protein is in a concentration of about 1,000 nM to about 2,000 nM.

15. A method of treating cancer comprising administering to a subject in need thereof:
 (i) the recombinant chimeric antigen receptor (CAR) fusion protein of claim 1; and
 (ii) a CAR immune cell.

16. The method of claim 15, wherein the CAR immune cell is prepared by treating an immune cell with the recombinant CAR fusion protein.

\* \* \* \* \*